United States Patent
Shima et al.

(10) Patent No.: US 6,291,464 B1
(45) Date of Patent: Sep. 18, 2001

(54) AMINOPIPERAZINE DERIVATIVES

(75) Inventors: Ichiro Shima, Moriyamachi; Kazuhiko Ohne, Tsukuba, both of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/355,960

(22) PCT Filed: Feb. 12, 1998

(86) PCT No.: PCT/JP98/00554

§ 371 Date: Aug. 17, 1999

§ 102(e) Date: Aug. 17, 1999

(87) PCT Pub. No.: WO98/35951

PCT Pub. Date: Aug. 20, 1998

(30) Foreign Application Priority Data

Feb. 17, 1997 (AU) .................................. PO 5125
Sep. 29, 1997 (AU) .................................. PO 9508

(51) Int. Cl.$^7$ ..................... A61K 31/495; C07D 295/26; C07D 295/30; C07D 295/32
(52) U.S. Cl. .................... 514/255.01; 514/590; 514/602; 514/605; 514/614; 514/617; 514/625; 544/382; 564/34; 564/37; 564/81; 564/82; 564/149; 564/151; 564/184; 564/215
(58) Field of Search ..................... 544/382; 514/255.01

(56) References Cited

U.S. PATENT DOCUMENTS 5,250,528 * 10/1993 Oku et al. ............................ 514/252

FOREIGN PATENT DOCUMENTS

1948993 * 6/1971 (DE) .
436734 * 7/1991 (EP) .

OTHER PUBLICATIONS

Ropenga et al., Chemical Abstracts, vol. 103:53776j, 1991.*
Ropenga et al., Chemical Abstracts, vol. 86:71797b, 1977.*
Grundzinski et al., chemical Abstracts, vol. 85;192321e, 1976.*
Strumillo et al., Chemical Abstracts, vol. 68:68621, 1968.*

* cited by examiner

*Primary Examiner*—Richard L. Raymond
(74) *Attorney, Agent, or Firm*—Oblon, Spivak, McClelland, Maier & Neustadt, P.C.

(57) ABSTRACT

This invention relates to new aminopiperazine derivatives having the potentiation of the cholinergic activity, etc., and represented by general formula [I].

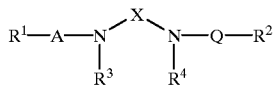

[I]

wherein
$R^1$ is lower alkyl, etc.,
R2 is aryl, etc.,
A is

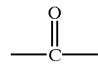

or —$SO_2$—,
Q is —N=CH—, etc.,
X is lower alkylene, etc., and
$R^3$ and $R^4$ are taken together to form lower alkylene, etc., and pharmaceutically acceptable salts thereof, to processes for preparation thereof and a pharmaceutical composition comprising the same.

6 Claims, No Drawings

AMINOPIPERAZINE DERIVATIVES

This application is a 371 of PCT/JP98/00554, filed Feb. 12, 1998.

TECHNICAL FIELD

This invention relates to new aminopiperazine derivatives and pharmaceutically acceptable salts thereof which are useful as a medicament.

BACKGROUND ART

Some aminopiperazine derivatives have been known as useful anti-amnesia or anti-dementia agents, for example, in PCT International Publication No. WO 91/01979.

DISCLOSURE OF INVENTION

This invention relates to new aminopiperazine derivatives and pharmaceutically acceptable salts thereof.

More particularly, it relates to new aminopiperazine derivatives and pharmaceutically acceptable salts thereof which have the potentation of the cholinergic activity, to processes for the preparation thereof, to a pharmaceutical composition comprising the same, and to a method for the treatment and/or prevention of disorders in the central nervous system for mammals, and more particularly to method for the treatment of amnesia, dementia, senile dementia and the like. Additionally, the object compound is expected to be useful as therapeutical and/or preventive agents for schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

One object of this invention is to provide new and useful aminopiperazine derivatives and pharmaceutically acceptable salts thereof which possess the potentation of cholinergic activity.

Another object of this invention is to provide processes for preparation of said aminopiperazine derivatives and salts thereof.

A further object of this invention is to provide a pharmaceutical composition comprising, as an active ingredient, said aminopiperazine derivatives and pharmaceutically acceptable salt thereof.

Still further object of this invention is to provide a therapeutic method for the treatment and/or prevention of aforesaid diseases in mammals, using said aminopiperazine derivatives and pharmaceutically acceptable salts thereof.

The aminopiperazine derivatives of this invention are new and can be represented by the following general formula [I]:

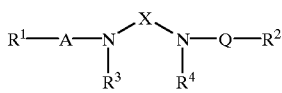

[I]

wherein
- $R^1$ is lower alkyl, lower alkenyl, lower alkynyl, cyclo(lower) alkyl, aryl, ar (lower) alkoxy, aryloxy, arylamino or a heterocyclic group, each of which may be substituted with suitable substituent(s); or acyl;
- $R^2$ is lower alkyl, lower alkenyl, lower alkynyl, cyclo(lower) alkyl, aryl, ar(lower)alkoxy, lower alkoxy, aryloxy or a heterocyclic group, each of which may be substituted with suitable substituent(s); or acyl;

A is

or $-SO_2-$,

Q is

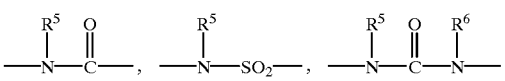

or $-N=CH-$ (wherein $R^5$ is hydrogen, lower alkyl, substituted-lower alkyl, aryl, acyl or a heterocyclic group, and $R^6$ is hydrogen or lower alkyl), X is lower alkylene optionally substituted with suitable substituent(s), and $R^3$ and $R^4$ are each hydrogen or lower alkyl, or are taken together to form lower alkylene optionally condensed with a cyclic hydrocarbon or a heterocyclic ring, provided that when
- $R^1$ is lower alkyl, aryl, ar(lower)alkoxy or a heterocyclic group, each of which may be substituted with halogen,
- $R^2$ is cyclo(lower)alkyl, aryl or ar(lower)alkyl, each of which may be substituted with halogen,
- X is ethylene and
- $R^3$ and $R^4$ are taken together to form ethylene;

then
1) Q is

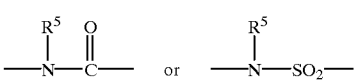

(wherein
$R^5$ is substituted-lower alkyl, aryl, acyl or a heterocyclic group), or 2) Q is

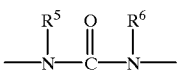

(wherein
$R^5$ is hydrogen, lower alkyl, substituted-lower alkyl, aryl, acyl or a heterocyclic group, and
$R^6$ is lower alkyl); or when $R^1$ is aryl which may be substituted with halogen;
X is ethylene;
$R^3$ and $R^4$ are taken together to form ethylene; and
$R^2$ is lower alkoxy, and
Q is

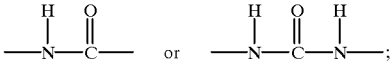

or
R² is aryl, and
Q is —N=CH—;
then A is
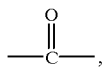
and pharmaceutically acceptable salts thereof.
The object compound [I] or its salt can be prepared by processes as illustrated in the following reaction schemes.
Process 1
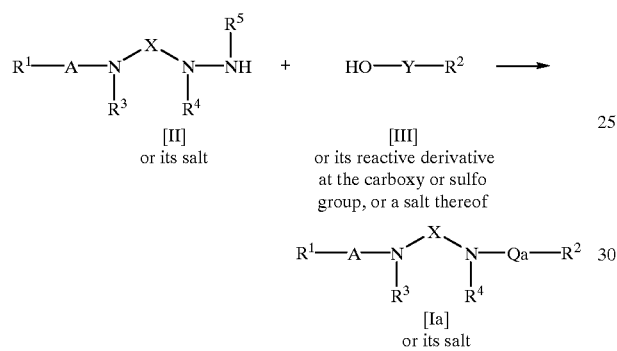
Process 2
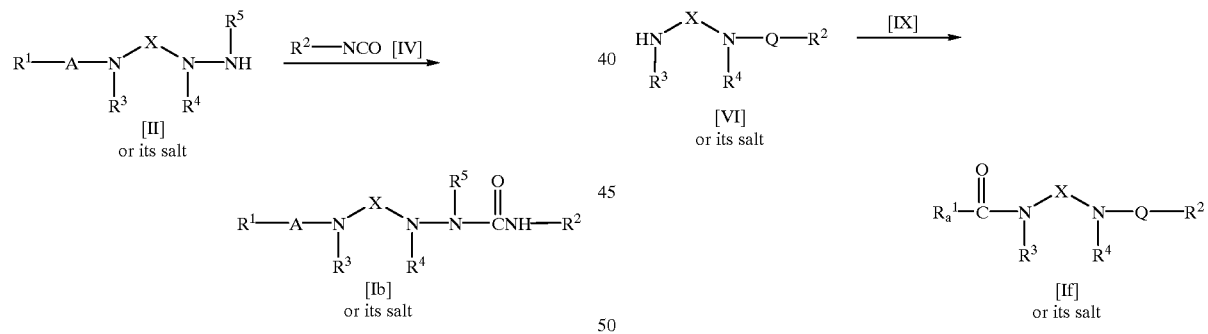
Process 3
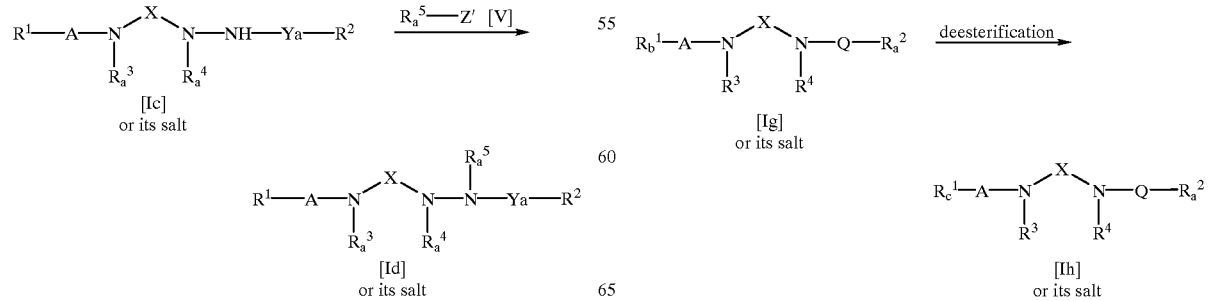
Process 4
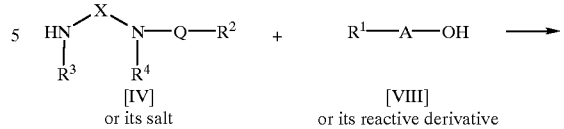
Process 5
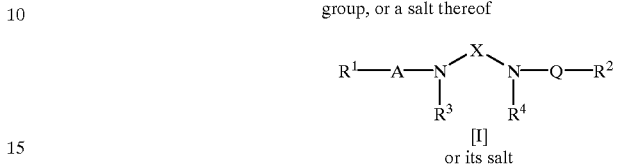
Process 6
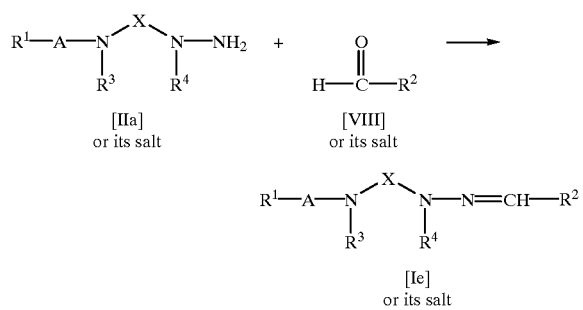
Process 7

Process 8

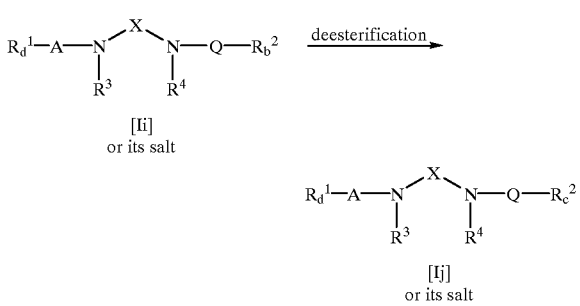

Process 9

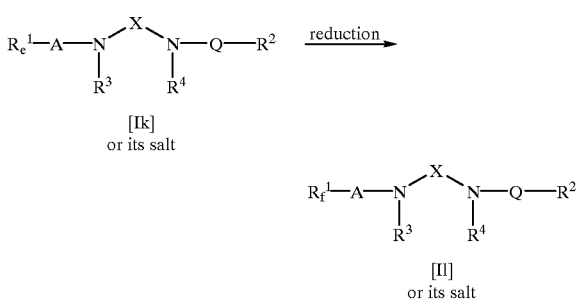

wherein $R^1$, $R^2$, $R^3$, $R^4$, $R^5$A, Q and X are each as defined above,

Y is

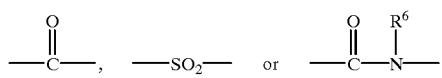

(wherein $R^6$ is as defined above),

Qa is

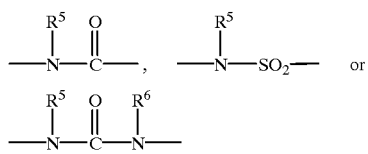

(wherein $R^5$ and $R^6$ are each as defined above), $R_a^5$ is lower alkyl or substituted-lower alkyl, $R_a^3$ and $R_a^4$ are each lower alkyl or are taken together to form lower alkylene, Ya is

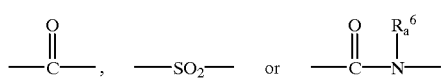

(wherein $R_a^6$ is lower alkyl),

Z is an acid residue, $R^7$ is aryl which may be substituted with suitable substituent(s), $R_a^1$ is arylamino which may be substituted with suitable substituent(s), $R_b^1$ is aryl which is substituted with esterified carboxy, $R_c^1$ is aryl which is substituted with carboxy, $R_a^2$ is aryl which may be substituted with halogen, $R_d^1$ is lower alkyl, $R_b^1$ is aryl which is substituted with esterified carboxy, $R_c^1$ is aryl which is substituted with carboxy, $R_e^1$ is aryl which is substituted with nitro, or $R_f^1$ is aryl which is substituted with amino.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

The lower moiety in the terms "lower alkenyl" and "lower alkynyl" is intended to mean a group having 2 to 6 carbon atoms.

The lower moiety in the term "cyclo(lower)alkyl" is intended to mean a group having 3 to 6 carbon atoms.

Suitable "lower alkyl" and lower alkyl moiety in the terms "substituted-lower alkyl", "ar(lower)alkyl", "halo (lower) alkyl", "lower alkylamino", "lower alkylsilyl", "lower alkylthio" and "lower alkylsulfonyl" may be a straight or branched $C_1$–$C_6$ alkyl such as methyl, ethyl, propyl, isopropyl, butyl, isobutyl, tert-butyl, pentyl, ethylpropyl, hexyl or the like, in which preferable one is methyl.

Suitable "lower alkenyl" may be a straight or branched $C_2$–$C_6$ alkenyl such as ethenyl, propenyl, butenyl, pentenyl, hexenyl, isopropenyl, butadienyl, pentadienyl, hexadienyl or the like, in which preferable one is ethenyl, propentyl or butadienyl.

Suitable "lower alkynyl" may be a straight or branched $C_2$–$C_6$ alkynyl such as ethynyl, propargyl, butynyl or the like, in which preferable one is ethynyl.

Suitable "cyclo(lower)alkyl" may be cyclo($C_3$–$C_6$)alkyl such as cyclopropyl, cyclobutyl, cyclopentyl or cyclohexyl, in which preferable one is cyclopropyl.

Suitable "aryl" and aryl moiety in the terms "ar (lower)alkoxy", "aryloxy", "arylamino", "arylsulfonyl", "aroyl" and "ar(lower)alkyl" may be phenyl, naphthyl, phenyl substituted with lower alkyl [e.g. tolyl, xylyl, mesityl, cumenyl, di(tert-butyl)phenyl, etc.] and the like, in which preferable one is phenyl or tolyl.

Suitable "ar(lower)alkyl" may be benzyl, phenethyl, phenylpropyl, benzhydryl, trityl and the like, in which preferable one is benzyl.

Suitable "lower alkylene" and lower alkylene moiety in the term "lower alkylenedioxy" may be a straight or branched $C_1$–$C_6$ alkylene such as methylene, ethylene, trimethylene, propylene, tetramethylene, pentamethylene, hexamethyiene, ethylethylene or the like, in which preferable one is methylene, ethylene or trimethylene.

Suitable "lower alkoxy" and lower alkoxy moiety in the terms "ar(lower)alkoxy" and "halo(lower)alkoxy" may be a straight or branched $C_1$–$C_6$ alkoxy such as methoxy, ethoxy, propoxy, isopropoxy, methylpropoxy, butoxy, isobutoxy, tert-butoxy, pentyloxy, hexyloxy or the like, in which preferable one is methoxy or tert-butoxy.

Suitable "ar(lower)alkoxy" may be benzyloxy, phenethyloxy, phenylpropoxy, benzhydryloxy, trityloxy and the like.

Suitable "halogen" and halo moiety in the term "halo (lower)alkyl" may be fluorine, chlorine, bromine and iodine, in which preferable one is fluorine.

Suitable "halo(lower)alkyl" may be lower alkyl substituted with one or more halogens such as chloromethyl, dichloromethyl, fluoromethyl, difluoromethyl, trifluoromethyl, pentachloroethyl or the like, in which preferable one is trifluoromethyl.

Suitable "halo(lower)alkoxyl" may be lower alkoxy substituted with one or more halogens such as chloromethoxy, dichloromethoxy, fluoromethoxy, difluoromethoxy, trifluoromethoxy, pentachloroethoxy or the like, in which preferable one is trifluoromethoxy.

Suitable "lower alkylamino" may be mono or di(lower alkylamino) such as methylamino, ethylamino, propylamino, isopropylamino, butylamino, tert-butylamino, isobutylamino, pentylamino, hexylamino, dimethylamino, diethylamino, dipopylamino, dibutylamino, diisopropylamino, dipentylamino, dihexylamino, N-methylethylamino or the like, in which preferable one is dimethylamino.

Suitable "lower alkylsilyl" may be mono, di, or tri(lower) alkylsilyl such as trimethylsilyl, dimethylsilyl, triethylsilyl or the like, in which preferable one is trimethylsilyl.

Suitable "lower alkylenedioxy" may be methylenedioxy, ethylenedioxy and the like, in which preferable one is methylenedioxy.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.; saturated 3 to 7-membered heteromonocyclic group containing 1 to 4 nitrogen atoms [e.g. pyrrolidinyl, imidazolidinyl, piperidyl, piperazinyl, homopiperazinyl, etc.]; unsaturated condensed heterocyclic group containing 1 to 5 nitrogen atoms, for example, indolyl, isoindolyl, indolizinyl, benzimidazolyl, quinolyl, isoquinolyl, imidazopyridyl, indazolyl, benzotriazolyl, tetrazolopyridazinyl [e.g. tetrazolo[1,5-b]pyridazinyl, etc.], quinoxalinyl, etc.; unsaturated 3 to 6-membered heteromonocyclic group containing an oxygen atom, for example, pyranyl, furyl, etc.; saturated 3 to 6-membered heteromonocyclic group containing an oxygen atom, for example, 1H-tetrahydropyranyl, tetrahydrofuranyl, etc.; unsaturated, 3 to 6-membered heteromonocyclic group containing 1 to 2 sulfur atoms, Lor example, thienyl, etc.; unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], oxazolinyl [e.g. 4:t 2-oxazolinyl, etc.], etc.; saturated 3 to 6-membered heteromonocyclic group containing 1 to 2 oxygen atoms and 1 to 3 nitrogen atoms [e.g. morpholinyl, etc.]; unsaturated condensed heterocyclic group containing 1 to 2 oxygen atoms and 1 to 3 nitrogen atoms [e.g. benzofurazanyl, benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.; saturated 3 to 6-membered heteromonocyclic group containing 1 to 2 sulfur atoms and 1 to 3 nitrogen atoms [e.g., thiazolidinyl, etc.]; unsaturated condensed heterocyclic group containing 1 to 2 sulfur atoms and 1 to 3 nitrogen atoms [e.g., benzothiazolyl, benzothiadiazolyl, etc.]; unsaturated condensed heterocyclic group containing 1 to 2 oxygen atoms [e.g. benzofuranyl, benzodioxolyl, chromanyl, etc.] and the like.

Said "heterocyclic group" may be substituted with lower alkyl as exemplified above, in which preferable one is thienyl, pyridyl, methylpyridyl, quinolyl, indolyl, quinoxalinyl, benzofuranyl or tetramethylchromanyl.

Suitable "acyl" and acyl moiety in the terms "acyloxy" and "acylamino" may be carboxy; esterified carboxy; carbamoyl optionally substituted with lower alkyl, ar(lower) alkyl, arylsulfonyl, lower alkylsulfonyl or a heterocyclic group; lower alkanoyl; aroyl; a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like.

The carbamoyl substituted with lower alkyl may be methylcarbamoyl, ethylcarbamoyl, propylcarbamoyl, dimethylcarbamoyl, diethylcarbamoyl, N-methyl-N-ethylcarbamoyl and the like.

The carbamoyl substituted with ar(lower)alkyl may be benzylcarbamoyl, phenethylcarbamoyl, phenylpropylcarbamoyl and the like, in which preferable one is benzylcarbamoyl.

The carbamoyl substituted with arylsulfonyl may be phenylsulfonylcarbamoyl, tolylsulfonylcarbamoyl and the like.

The carbamoyl substituted with lower alkylsulfonyl may be methylsulfonylcarbamoyl, ethylsulfonylcarbamoyl and the like.

The carbamoyl substituted with a heterocyclic group may be one substituted with a heterocyclic group as mentioned above.

The lower alkanoyl may be substituted or unsubstituted one such as formyl, acetyl, propionyl, butyryl, isobutyryl, valeryl, isovaleryl, pivaloyl, hexanoyl, trifluoroacetyl or the like.

The aroyl may be benzoyl, naphthoyl, toluoyl, di(tertbutyl)benzoyl and the like, in which preferable one is benzoyl.

The heterocyclic moiety in the term "a heterocycliccarbonyl" may be one mentioned above as a heterocyclic group.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

Suitable "cyclic hydrocarbon" may be a saturated or unsaturated cyclic hydrocarbon such as cyclopentane, cyclohexane, benzene, naphthalene, indan, indene or the like.

Suitable "substituted-lower alkyl" may be lower alkyl substituted with halogen, aryl, acyl, lower alkoxy, aryloxy and the like, in which preferable one is benzyl.

Suitable "heterocyclic ring" may be one which is a heterocyclic group, as mentioned above, added by hydrogen.

Preferred "suitable substituent" as the substituent of lower alkyl, lower alkenyl, lower alkynyl, cyclo(lower)alkyl, aryl, ar(lower)alkoxy, aryloxy, arylamino or a heterocyclic group for $R^1$ may be halo(lower)alkyl, halo(lower)alkoxy, lower alkenyl, lower alkynyl, lower alkylamino, acylamino, acyl, lower alkylsilyl, lower alkoxy, aryl, lower alkylenedioxy, acyloxy, hydroxy, nitro, amino, cyano, aryloxy, lower alkylthio and the like.

Preferred "lower alkyl which may be substituted with suitable substituent(s)" for $R^1$ may be lower alkyl optionally substituted with lower alkoxy, in which more preferable one is methoxymethyl.

Preferred "lower alkenyl which may be substituted with suitable substituent(s)" for $R^1$ may be lower alkenyl optionally substituted with aryl, in which more preferable one is propenyl, butadienyl or styryl.

Preferred "lower alkynyl which may be substituted with suitable substituent(s)" for $R^1$ may be lower alkynyl optionally substituted with aryl, in which more preferable one is ethynyl or phenylethynyl.

Preferred "cyclo(lower)alkyl which may be substituted with suitable substituent(s)" for $R^1$ may be cyclopropyl.

Preferred "aryl which may be substituted with suitable substituent(s)" for $R^1$ may be aryl optionally substituted with halo(lower)alkyl, halo(lower)alkoxy, lower alkenyl, lower alkynyl, lower alkylamino, lower alkylsilyl, lower alkoxy, lower alkylenedioxy, hydroxy, nitro, amino, cyano, aryl, aryloxy, acyl, acylamino or lower alkylthio, in which more preferable one is phenyl optionally substituted with trifluoromethyl, trifluoromethoxy, ethenyl, ethynyl, dimethylamino, trimethylsilyl, methoxy, methylenedioxy hydroxy, nitro, amino, cyano, phenyl, phenoxy, carboxy, methoxycarbonyl, methylsulfonyl, acetamido or methylthio.

Preferred "ar(lower)alkoxy which may be substituted with suitable substituent(s)" for $R^1$ may be ar(lower)alkoxy, in which more preferable one is benzyloxy, phenethyloxy, phenylpropoxy, benzhydryloxy or trityloxy.

Preferred "aryloxy which may be substituted with suitable substituent(s)" for R may be aryloxy, in which more preferable one is phenoxy.

Preferred "arylamino which may be substituted with suitable substituent(s)" for $R^1$ may be arylamino, in which more preferable one is arylamino.

Preferred "a heterocyclic group which may be substituted with suitable substituent(s)" for $R^1$ may be pyridyl, methylpyridyl or (hydroxy)tetramethylchromanyl.

Preferred "acyl" for $R^1$ may be aroyl, in which more preferable one is benzoyl.

Preferred "suitable substituent" as the substituent of lower alkyl, lower alkenyl, lower alkynyl, cyclo(lower)alkyl, aryl, ar(lower)alkoxy, lower alkoxy, aryloxy or a heterocyclic group for $R^2$ may be halo(lower)alkyl, lower alkenyl, lower alkynyl, lower alkylamino, acyl, lower alkylsilyl, lower alkoxy, aryl, lower alkylenedioxy, acyloxy, hydroxy, cyano, aryloxy, acylamino, nitro, halogen, halo(lower)alkoxy, lower alkylthio and the like.

Preferred "lower alkyl which may be substituted with suitable substituent(s)" for $R^2$ may be lower alkyl substituted with aryl or aryl and hydroxy, in which more preferable one is benzyl or phenylhydroxymethyl.

Preferred "lower alkenyl which may be substituted with suitable substituent(s)" for $R^2$ may be lower alkenyl optionally substituted with aryl, in which more preferable one is styril.

Preferred "lower alkynyl which may be substituted with suitable substituent(s)" for $R^2$ may be lower alkynyl optionally substituted with aryl, in which more preferable one is ethynyl or phenylethynyl.

Preferred "aryl which may be substituted with suitable substituent(s)" for $R^2$ may be aryl optionally substituted with halo(lower)alkyl, lower alkenyl, lower alkynyl, lower alkylamino, lower alkoxy, lower alkylenedioxy, hydroxy, cyano, aryl, aryloxy, acyl, acylamino, nitro, halogen, halo (lower)alkoxy or lower alkylthio, in which more preferable one is phenyl optionally substituted with trifluoromethyl, ethenyl, ethynyl, dimethylamino, methoxy, methylenedioxy, hydroxy, cyano, phenyl, phenoxy, carboxy, methoxycarbonyl, methylsulfonyl, acetamido, nitro, fluoro, trifluoromethoxy or methylthio.

Preferred "aryloxy which may be substituted with suitable substituent(s)" for $R^2$ may be aryloxy, in which more preferable one is phenoxy.

Preferred "a heterocyclic group which may be substituted with suitable substituent(s)" for $R^2$ may be quinolyl, thienyl, pyridyl, methylpyridyl, (hydroxy)tetramethylchromanyl, fluoroindolyl, quinoxalinyl or (chloro)phenylbenzofuranyl.

Preferred "acyl" for $R^2$ may be aroyl, in which more preferable one is benzoyl.

Preferred "aryl" for $R^5$ in Q may be phenyl or tolyl.

Preferred "substituted-lower alkyl" for $R^5$ in Q may be lower alkyl substituted with aryl, in which more preferable one is benzyl.

Preferred "a heterocyclic group" for $R^5$ in Q may be pyridyl.

Preferred "lower alkyl" for $R^6$ in Q may be methyl.

Preferred "suitable substituent" as the substituent of lower alkylene for X may be oxo, lower alkyl, hydroxy(lower) alkyl or acyl, in which more preferable one is oxo, dioxo, methyl, dimethyl, hydroxymethyl or benzylcarbamoyl.

Preferred "lower alkylene" for X may be methylene, ethylene or trimethylene.

Preferred "lower alkyl" for $R^3$ and $R^4$ may be methyl.

Preferred "lower alkylene which $R^3$ and $R^4$ are taken together to form" may be ethylene or trimethylene.

Preferred "a cyclic hydrocarbon with which lower alkylene is condensed" may be benzene.

Suitable pharmaceutically acceptable salts of the object compound [I] are conventional non-toxic salts and include acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a salt with an amino acid [e.g. aspartic acid salt, glutamic acid salt, etc.], a metal salt such as an alkali metal salt [e.g. sodium salt, potassium salt, etc.] and alkaline earth metal salt [e.g. calcium salt, magnesium salt, etc.] and the like.

The processes for preparing the object compound [I] are explained in detail in the following.

Process 1

The compound [Ia] or its salt can be prepared by reacting a compound [II] or its salt with a compound [III] or its reactive derivative at the carboxy or sulfo group, or a salt thereof.

Suitable salt of the compounds [Ia] and [II] may be the same as those exemplified for the compound [I].

Suitable salts of the compound [III] and its reactive derivative at the carboxy or sulfo group may be metal salt or alkaline earth metal salt as exemplified for the compound [I].

Suitable reactive derivative at the carboxy or sulfo group of the compound [III] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as substituted or unsubstituted lower alkyl ester [e.g. methyl ester, ethyl ester, propyl ester, hexyl ester, trichloromethyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxybenzotriazole, 1-hydroxy-6-chloro-1H-benzotriazole, or the like. These reactive derivatives can be optionally selected according to the kind of the compound [III] to be used.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvent may be used in a mixture with water.

When the compound [III] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction temperature is not critical, and the reaction can be carried out under cooling to heating.

Process 2

The compound [Ib] or its salt can be prepared by reacting a compound [II] or its salt with a compound [IV].

Suitable salts of the compounds [Ib] and [II] may be the same as those exemplified for the compound [I].

This reaction is usually carried out in a solvent such as dioxane, tetrahydrofuran, benzene, chloroform, methylene chloride or any other organic solvent which does not adversely influence the reaction.

The reaction temperature is not critical, and the reaction is usually carried out under cooling to warming.

Process3

The compound [Id] can be prepared by reacting a compound [Ic] or its salt with a compound [V].

Suitable salts of the compounds [Ic] and [Id] may be the same as those exemplified for the compound [I].

The present reaction is preferably carried out in the presence of base such as an alkali metal (e.g. lithium, sodium, potassium, etc.), alkaline earth metal (e.g. calcium, of etc.), alkali metal hydride (e.g. sodium hydride, etc.), alkaline earth metal hydride (e.g. calcium hydride, etc.) and the like.

This reaction is usually carried out in a solvent such as N,N-dimethylformamide, diethyl ether, tetrahydrofuran, dioxane, benzene, toluene or any other solvent which does not adversely influence the reaction.

The reaction temperature is not critical, and the reaction is usually carried out under cooling to heating.

Process 4

The compound [I] or its salt can be prepared by reacting a compound [VI] or its salt with a compound [VII] or its reactive derivative at the carboxy or sulfo group, or a salt thereof.

Suitable salt of the compound [VI] may be the same as those exemplified for the compound [I].

Suitable salts of the compound [VII] and its reactive derivative at the carboxy or sulfo group may be metal salt or alkaline earth metal salt as exemplified for the compound [I].

This reaction can be carried out in substantially the same manner as Process 1, and therefore the reaction mode and reaction condition [e.g. solvent, reaction temperature, etc.] of this reaction are to be referred to those as explained in Process 1.

Process 5

The compound {Ie] or its salt can be prepared by reacting a compound [IIa] or its salt with a compound [VIII] or its salt.

Suitable salt of the compound [IIa] may be the same as those exemplified for the compound [I].

Suitable salts of the compounds [lIe] and [VIII] may be metal salt or alkaline earth metal salt as exemplified for the compound [I].

This reaction is also preferably carried out in the presence of tri(lower)alkylamine [e.g. trimethylamine, triethylamine, etc.].

The reaction is usually carried out in a conventional solvent which does not adversely influence the reaction such as water, dioxane, an alcohol [e.g. methanol, ethanol, etc.], tetrahydrofuran or a mixture thereof.

The reaction temperature is not critical and the reaction is usually carried out under warming to heating.

Process 6

The compound [If] or its salt can be prepared by reacting a compound [VI] or its salt with a compound [IX].

Suitable salts of the compounds [If] and [VI] may be the same as those exemplified for the compound [I].

This reaction can be carried out in substantially the same manner as Process 2, and therefore the reaction mode and reaction condition [e.g. solvent, reaction temperature, etc.] of this reaction are to be referred to those as explained in Process2.

Process 7

The compound [Ih] or its salt can be prepared by subjecting a compound [Ig] or its salt to deesterification reaction.

Suitable salts of the compounds [Ig] and [Ih] may be the same as those exemplified for the compound [I].

The reaction is carried out in accordance with a conventional method such as hydrolysis or the like.

The hydrolysis is preferably carried out in the present of a base or an acid including Lewis acid. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2] octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], xylene, diethylene glycol monomethyl ether, methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

Process 8

The compound [Ij] or its salt can be prepared by subjecting a compound [Ii] or its salt to deesterification reaction.

Suitable salts of the compounds [Ii] and [Ij] may be the same as those exemplified for the compound [I].

This reaction can be carried out in substantially the same manner as Process 7, and therefore the reaction mode and reaction condition [e.g. solvent, reaction temperature, etc.] of this reaction are to be referred to those as explained in Process 7.

Process 9

The compound [II] or its salt can be prepared by reducing the compound [Ik] or its salt.

Suitable salts of the compounds [Ik] and [Il] may be the same as those exemplified for the compound [I].

The reaction may Include chemical reduction and catalytic reduction, which are carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, an alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reaction is preferably carried out under warming to heating.

The compounds obtained by the above processes can be isolated and purified by a conventional method such as pulverization, recrystallization, column chromatography, reprecipitation, or the like.

It is to be noted that the compound [I] and the other compounds may include one or more stereoisomer(s) such as optical isomer(s) or geometrical isomers) due to asymmetric carbon atom(s) and double bond(s), and all of such isomers and mixture thereof are included within the scope of this invention.

Additionally, it is to be noted that any solvate [e.g. enclosure compound (e.g. hydrate, etc.)] of the compound or a pharmaceutically acceptable salt thereof [I] is also included within the scope of this invention.

The object compound [I] and pharmaceutically acceptable salts thereof possess strong potentiation of the cholinergic activity, and are useful for the treatment of disorders in the central nervous system for mammals, and more particularly of amnesia, dementia, senile dementia and the like. Additionally, the object compound is expected to be useful as therapeutical and/or preventive agents for schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

In order to illustrate the usefulness of the object compound [I], the pharmacological data of the compound [I] is shown in the following.

Test

Penile erection in rat (This test was carried out according to a similar manner to that described in Jpn. J. Pharmacol., Vol. 64, 147–153 (1994))

(i) Method

Male Fischer 344 rats at the age of 8 weeks (n=7) were used. All rats were handled 3 minutes a day for three successive days before the tests. The rats were tested in groups of six and various doses of the test compound were given in semi-randomized order. The test compounds were suspended in 0.5% methyl-cellulose immediately before use, and given intraperitoneally in a volume of 1 ml/kg just before the start of test. Immediately after injunction, each rat was placed in a perspex box (25×25×35 cm) and its behavior was observed for 60 minutes, during which time the number of penile erections was counted. A mirror was situated behind each box to facilitate of the rat. Data was expressed as a mean number.

(ii) Test Result

| Test Compound (Example No.) | Dose (mg/kg) | Penile Erection (number/hr) |
|---|---|---|
| 2 | 1 | 2.57 |
| 3-2) | 0.1 | 1.71 |
| 14-3) | 0.32 | 1.57 |

It is clear that the compound having the above-mentioned activity ameliorates the memory deficits (i.e. amnesia, dementia, senile dementia, etc.) from the description in The Journal of Pharmacology and Experimental Therapeutics, Vol. 279, No. 3, 1157–1173 (1996). Further, it is expected that the compound having the above-mentioned activity is useful as therapeutical and/or preventive agent for aforesaid diseases from some patent applications filed before this patent application.

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral or parenteral administration. The pharmaceutical preparations may be capsules, tablets, dragees, granules, suppositories, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

Preparation 1

To a stirred solution of 1-nitrosohomopiperazine (4.174 g) and triethylamine (9 ml) in dichloromethane (25 ml) was added dropwise benzyloxycarbonyl chloride (5 ml) at 0° C. The reaction mixture was stirred at ambient temperature for 1 hour. The reaction mixture was diluted with water and separated. The organic layer was washed with water (×2), brine, dried over magnesium sulfate and concentrated to give 1-benzyloxycarbonyl-4-nitrosohomopiperazine (6.0 g). This product was used for the next step without purification.

Preparation 2

To a slurry of rac-ethyl 1-acetylpiperazine-2-carboxylate (0.5 g) in water (5 ml) was added concentrated hydrochloric acid (1.5 ml) dropwise below 25° C. A solution of sodium nitrite (380 mg) in water (2 ml) was added dropwise at 0° C. The mixture was stirred at 0° C. for 2 hours. A solution of sodium hydroxide (726 mg) in water (10 ml) was added dropwise at 0° C. The water was evaporated off to give crude rac-1-acetyl-2-carboxy-4-nitrosopiperazine (1.0 g). The crude product, benzylamine (0.6 ml) and 1-hydroxybenzotriazole (1.351 g) in N,N-dimethylformamide (5 ml) was added N-ethyl-N'-(3-dimethylaminopropyl)carbodiimide hydrochloride (1.92 g) at 0° C. The reaction mixture was stirred at ambient temperature for 4 hours. The reaction mixture was poured into the mixture of ethyl acetate and brine. The organic layer was combined, dried over magnesium sulfate, and concentrated to give rac-N-benzyl-1-acetyl-4-nitrosopiperazine-2-carboxamide (655 mg). This product was used for next step without purification.

Preparation 3

To a slurry of (S)-1-acetyl-2-methylpiperazine (424 mg) in water (2.5 ml) was added concentrated hydrochloric acid (0.9 ml) dropwise below 25° C. A solution of sodium nitrite (227 mg) in water (2 ml) was added dropwise at 0° C. The mixture was stirred at 0° C. for 2 hours. A solution of sodium hydroxide (409 mg) in water (6 ml) was added dropwise at 0° C. The mixture was extracted with chloroform, washed with water, dried and evaporated to give (S)-1-acetyl-2-methyl-4-nitrosopiperazine (350 mg). This product was used for next step without purification.

Preparation 4

To a mixture of 1-benzyloxycarbonyl-4-nitrosohomopiperazine (1.0 g) in water (2.0 ml) and acetic acid (1.09 ml) was added zinc powder (745 mg) at 8–13° C. (exothermic reaction) with ice-water cooling bath. After removal of the bath, the temperature was raised till 55° C. and the reaction mixture was additionally stirred at 30–40° C. for 1 hour. Acetic acid (1.09 ml) and zinc powder (745 mg) was added to the reaction mixture and stirred at 40° for 1 hour. After cooling, zinc residue was filtered off and washed with methanol (5 ml) on the Celite. The combined filtrate was added into dichloromethane (10 ml) and sodium hydroxide (1.6 g) in water (5 ml) below 35° C. The resulting precipitate was filtered off with Celite and the residue was washed with dichloromethane (20 ml). The combined filtrate was dried over magnesium sulfate and filtered. The filtrate was condensed in vacuo to give 1-amino-4-benzyloxycarbonylhomopiperazine (690 mg). This product was used for next step without further purification.

Preparation 5

To a mixture of rac-N-benzyl-1-acetyl-4-nitrosopiperazine-2-carboxamide (655 mg) in water (2 ml) and acetic acid (0.65 ml) was added zinc powder (443 mg) as portions during the period of 2 hours at 8–13° C. (exothermic reaction) with ice-water cooling bath. After removal of the bath, the temperature was raised till 55° C. and the reaction mixture was additionally stirred at 30–40° C. for 2 hours. The zinc residue was filtered off and washed with methanol (50 ml) on the Celite. The combined filtrate was added into dichloromethane (40 ml) and sodium hydroxide (460 mg) in water (6 ml) below 35° C. The resulting precipitate was filtered off with Celite and the residue was washed with chloroform (50 ml). The combined filtrate was washed with water, dried over magnesium sulfate and concentrated to give rac-N-benzyl-1-acetyl-4-aminopiperazine-2-carboxamide (274 mg). This product was used for next step without purification.

Preparation 6

To a mixture of (S)-1-acetyl-2-methyl-4-nitrosopiperazine (350 mg) in water (2 ml) and acetic acid (0.59 ml) was added zinc powder (401 mg) as portions during the period of 2 hours at 8–13° C. (exothermic reaction) with ice-water cooling bath. After removal of the bath, the temperature was raised till 55° C. and the reaction mixture was additionally stirred at 45° C. for 2 hours. The zinc residue was filtered off and washed with methanol (10 ml) on the Celite. The combined filtrate was added into dichloromethane (40 ml) and sodium hydroxide (409 mg) in water (6 ml) below 35° C. The resulting precipitate was filtered off with Celite and the residue was washed with chloroform (50 ml). The combined filtrate was washed with water, dried over magnesium sulfate and concentrated to give (S)-1-acetyl-4-amino-2-methylpiperazine (320 mg). This product was used for next step without purification.

Preparation 7

To a stirred solution of rac-ethyl 4-benzoyloxycarbonylpiperazine-2-carboxylate (4 g) and triethylamine (5.1 ml) in dichloromethane (50 ml) was added acetic anhydride (1.72 ml) at 0° C. The mixture was stirred at ambient temperature for 3 hours, diluted with chloroform and washed with 1N hydrochloric acid, water, saturated aqueous solution of sodium hydrogen carbonate, water, brine, dried over magnesium sulfate and concentrated. The residue was purified by flash column chromatography eluting with a mixture of ethyl acetate and n-hexane (2:1) to give rac-ethyl 1-acetyl-4-benzyloxycarbonylpiperazine-2-carboxylate (4.63 g).

NMR (DMSO-$d_6$, δ): 1.07 (3H, br s), 1.98 (1H, s), 2.07 (2H, s), 3.15–3.38 (2H, m), 3.75–3.92 (2H, m), 4.00–4.10 (2H, m), 4.35–4.50 (2H, m), 4.85 (1/3H, s), 4.98 (2/3H, d, J=5 Hz), 5.07 (2H, s), 7.30–7.40 (5H, m)

Preparation 8

To a stirred solution of (S)-1-tert-butoxycarbonyl-2-methyl-3-oxo-4-benzylpiperazine (1.0 g) in tetrahydrofuran (15 ml) was added borane-dimethylsulfide complex (0.49 ml) at 0° C. under nitrogen atmosphere. After stirring at 45° C. for 1.5 hours, borane-dimethylsulfide complex (0.46 ml) was added and the reaction mixture was stirred at 45° C. for another 2 hours. After cooled to 0° C., the reaction mixture was quenched with methanol. After evaporation of the solvent, the residue was purified by flash column chromatography eluting with a mixture of ethyl acetate and n-hexane (1:8) to give (S)-1-tert-butoxycarbonyl-2-methyl-4-benzylpiperazine (934 mg).

NMR (CDCl$_3$, δ): 1.34 (3H, d, J=7 Hz), 1.46 (9H, s), 2.00 (1H, ddd, J=10, 10, 5 Hz), 2.12 (1H, dd, J=10, 5 Hz), 2.59 (1H, dt, J=8, 2, 2 Hz), 2.76 (1H, dd, J=8, 2 Hz), 3.11 (1H, ddd, J=10, 10, 5 Hz), 3.47 (2H, ABq, J=15, 14.5 Hz), 3.81 (1H, d, J=14.5 Hz), 4.13–4.22 (1H, m), 7.25–7.35 (5H, m)

Preparation 9

To a stirred solution of (S)-1-tert-butoxycarbonyl-2-methyl-4-benzylpiperazine (864 mg) in methanol (5 ml) was added concentrated hydrochloric acid (0.94 ml). The reaction mixture was stirred at 50° C. for 1 hour. After cooling, the solvent was evaporated off. The residue was made to alkali with 1N aqueous solution of sodium hydroxide and extracted with ethyl acetate (×3). The combined organic layer was dried over magnesium sulfate and concentrated to give (S)-1-benzyl-3-methylpiperazine (588 mg).

NMR (DMSO-$d_6$, δ): 1.00 (3H, d, J=7 Hz), 1.62–1.70 (1H, m), 1.97–2.04 (1H, m), 2.73–2.95 (5H, m), 3.49 (2H, s), 7.27–7.31 (5H, m)

Preparation 10

To a stirred solution of (S)-1-benzyl-3-methylpiperazine (588 mg) and triethylamine (0.47 ml) in dichloromethane (5 ml) was added acetic anhydride (0.32 ml) at 0° C. The reaction mixture was stirred at ambient temperature for 4 hours. Methanol was added to this solution and evaporated. The residue was taken up in ethyl acetate and washed with water and brine. The organic layer was dried over magnesium sulfate and concentrated. The residue was purified by column chromatography eluting with a mixture of ethyl acetate and n-hexane (2:1) to give (S)-1-acetyl-4-benzyl-2-methylpiperazine (660 mg).

NMR (CDCl$_3$, δ): 1.25 (4/3H, d, J=7 Hz), 1.36 (5/3H, d, J=7 Hz), 2.07 (4/3H, s), 2.10 (5/3H, s), 1.95–2.19 (2H, m), 3.39–3.58 (3H, m), 2.67 (1H, d, J=13 Hz), 2.79–2.87 (1H, m), 2.96 (1/2H, t, J=15 Hz), 3.92 (1/2H, s), 4.39 (1/2H, d, J=15 Hz), 4.72 (l/2H, s), 2.70–2.79 (4H, m), 2.92–3.00 (4H, m), 5.44 (1H, s)

Preparation 11

To a solution of 25% hydrogen bromide-acetic acid (1.5 ml) and anisole (0.09 ml) was added N-(4-benzyloxycarbonyl-1-homopiperazinyl)-p-fluorobenzamide (529 mg) dropwise for 3 minutes under nitrogen atmosphere. The reaction mixture was stirred at ambient temperature for 3.5 hours and diluted with diethyl ether. The resulting precipitate was collected and washed with diethyl ether to give N-(l-homopiperazinyl)-4-fluorobenzamide hydrobromide (606 mg). This product was used for next step without further purification.

Preparation 12

4N Hydrogen chloride-ethyl acetate (250 ml) was added into N-(4-acetyl-1-piperazine)-tert-butoxycarboxamide (16 g), and the mixture was stirred at ambient temperature for 4 hours. The precipitate was collected and washed with ethyl acetate to give 1-acety-4-aminopiperazine dihydrochloride (14 g).

mp: 155–157° C.

NMR (CDCl$_3$, δ): 2.03 (3H, s), 2.78–3.02 (4H, m), 3.39–3.67 (4H, m)

Preparation 13

To a solution of rac-ethyl 1-acetyl-4-benzyloxycarbonylpiperazine-2-carboxylate (346 mg) in methanol (10 ml) was added 10% palladium on carbon (110 mg), and the mixture was stirred at ambient temperature under 1 atm for 5 hours. Palladium on carbon was filtered off on Celite and the filtrate was concentrated to give an oil which was purified by flash column chromatography eluting with a mixture of methanol and ethyl acetate (1:10) to give rac-ethyl 1-acetylpiperazine-2-crboxylate (160 mg).

NMR (CDCl$_3$, δ): 1.28 (3H, t, J=7 Hz), 2.15 (3H, s), 2.70–3.07 (4H, m), 3.43–3.64 (3H, m), 4.18–4.42 (2H, m), 5.19 (1H, d, J=5 Hz)

Preparation 14

(S)-1-Acetyl-2-methyl-4-benzylpiperazine (1.87 g) was hydrogenated over palladium hydroxide (600 mg) at ambient temperature for 3 hours. The catalyst was filtered off and the solvent was evaporated off. The residue was purified by column chromatography eluting with a mixture of methanol and chloroform (1:5) to give 440 mg of (S)-1-acetyl-2-methylpiperazine (440 mg).

NMR (CDCl$_3$, δ): 1.23 (4/3H, d, J=7 Hz), 1.34 (5/3H, d, J=7 Hz), 2.08 (4/3H, s), 2.11 (5/3H, s), 2.63–2.95 (3H, m), 3.01 (1H, d, J=13 Hz), 3.25–3.48 (1H, m), 3.90 (0.5H, s), 4.36 (1H, d, J=15 Hz), 4.70 (0.5H, s)

Preparation 15

To a solution of N-(4-benzyloxycarbonyl-1-piperazinyl)-tert-butoxycarboxamide (28 g) in methanol (250 ml) was added 10% palladium on carbon (5 g), and the mixture was stirred at ambient temperature under 3 atm of hydrogen for 1 hour. Palladium on carbon was filtered off and the filtrate was concentrated to give N-(1-piperazinyl)-tert-butoxycarboxamide (17.6 g).

mp: 183–184° C.

NMR (CDCl$_3$, δ): 1.45 19H, s), 2.70–2.79 (4H, m), 2.92–3.00 (4H, m), 5.44 (1H, s)

EXAMPLE 1

1) To a solution of 25% hydrogen bromide-acetic acid (30 ml) and anisole (1.6 ml) was added N-(4-benzyloxycarbonyl-1-piperazinyl)-p-fluorobenzamide (10 g) dropwise for 15 minutes under nitrogen atmosphere. The reaction mixture was stirred at ambient temperature for 3 hours. The resulting precipitate was collected and washed with diethyl ether (10 ml) to give N-piperazinyl-p-fluorobenzamide hydrobromide (10.2 g) as white hydroscopic solid.

2) To a solution of N-piperazinyl-p-fluorobenzamide hydrobromide (500 mg) in 1N aqueous solution of sodium hydroxide (5 ml) and dioxane (5 ml) was added cyclopropanecarbonyl chloride (0.3 ml) at ambient temperature, and the solution was stirred at (he same temperature for 2 hours. After removal of the solvent in vacuo, the residue was dissolved into ethyl acetate and washed with brine (×2). The organic layer was separated, dried over magnesium sulfate, and concentrated. The residue was recrystallized from 20% ethanol-water to give N-(4-cyclopropanecarbonyl-1-piperazinyl)-p-fluorobenzamide (0.20 g).

mp: 183–184° C.

NMR (CDCl$_3$, δ) 0.75–0.82 (2H, m), 0.96–1.02 (2H, m), 1.70–1.80 (1H, m), 2.86–3.06 (4H, br m), 3.75–3.92 (4H, br s), 7.01 (1H, br s), 7.08–7.15 (2H, m), 7.72–7.83 (2H, m)

MASS (ES+) (m/z): 292

EXAMPLE 2

To a solution of N-piperazinyl-p-fluorobenzamide hydrobromide (500 mg) in 1N aqueous solution of sodium hydroxide (5 ml) and dioxane (5 ml) was added 2-(trifluoromethyl)benzoyl chloride (0.363 ml) at ambient temperature, and the solution was stirred at the same temperature for 2 hours. After removal of the solvent in vacuo, the residue was dissolved into ethyl acetate and washed with brine (×2). The organic layer was separated, dried over magnesium sulfate, and concentrated. The residue was recrystallized from ethyl acetate—diethyl ether to give N-[4-o-(trifluoromethyl)benzoyl-1-piperazinyl]-p-fluorobenzamide (0.39 g).

mp: 204–205° C.

NMR (CDCl$_3$, δ): 2.71–2.83 (1H, m), 2.85–3.04 (2H, m), 3.11–3.23 (1H, m), 3.31–3.42 (2H, m), 3.81–3.93 (1H, m), 4.08–4.22 (1H, m), 7.00 (1H, br s), 7.12 (2H, t, J=7.5 Hz), 7.36 (1H, d, J=7.5 Hz), 7.54 (1H, t, J=7.5 Hz), 7.62 (1H, t, J=7.5 Hz), 7.70–7.80 (3H, m)

MASS (ES+) (m/z): 396

EXAMPLE 3

The following compounds were obtained according to a similar manner to that of Example 2.

1) N-(4-p-Methoxybenzoyl-1-piperazinyl)-p-fluorobenzamide mp: 214–215° C.

NMR (CDCl$_3$, δ): 2.71–2.83 (1H, m), 2.85–3.04 (2H, m), 3.11–3.23 (1H, m), 3.31–3.42 (2H, m), 3.81–3.93 (1H, m), 4.08–4.22 (1H, m), 7.00 (1H, br s), 7.12 (2H, t, J=7.5 Hz), 7.36 (1H, d, J=7.5 Hz), 7.54 (1H, t, J=7.5 Hz), 7.62 (1H, t, J=7.5 Hz), 7.70–7.80 (3H, m)

MASS (ES+) (m/z): 358

2) N-(4-Piperonyloyl-1-piperazinyl)-p-fluorobenzamide mp: 169–171° C.

NMR (CDCl$_3$, δ): 3.10 (4H, br s), 3.83 (4H, br s), 6.00 (2H, s), 6.78–6.86 (1H, m), 6.88–6.97 (2H, m), 7.72–7.83 (2H, m)

MASS (ES+) (m/z): 372

3) N-[4-(p-Trifluoromethoxy)benzoyl-1-piperazinyl]-p-fluorobenzamide mp: 204–205° C.

NMR (CDCl$_3$, δ): 3.07 (4H, br s), 3.57–4.05 (4H, m), 7.12 (2H, dd, J=8, 8 Hz), 7.27 (2H, d, J=8 Hz), 7.48 (2H, d, J=8 Hz), 7.71–7.81 (2H, m) MASS (ES+) (m/z): 412

4) N-(4-Phenoxycarbonyl-1-piperazinyl)-p-fluorobenzamide mp: 214–215° C.

NMR (CDCl$_3$, δ): 3.18 (4H, br s), 3.82 (2H, br s), 3.91 (2H, br s), 7.06–7.26 (5H, m), 7.32–7.41 (2H, m), 7.73–7.85 (2H, m)

EXAMPLE 4

To a solution of N-piperazinyl-p-fluorobenzamide hydrobromide (300 mg) in 1N aqueous solution of sodium hydroxide (3 ml) and dioxane (3 ml) was added crotonic anhydride (0.22 ml) at ambient temperature, and the solution was stirred at the same temperature for 1 hour. After removal of the solvent in vacuo, the residue was dissolved into ethyl acetate and washed with brine (×2). The organic layer was separated, dried over magnesium sulfate, and concentrated. The residue was crystallized from ethyl acetate-diethyl ether to give N-(4-crotonoyl-1-piperazinyl)-p-fluorobenzamide (0.15 g).

mp: 191–193° C.

NMR (CDCl$_3$, δ): 1.88 (3H, d, J=7.5 Hz), 3.00 (4H, br s), 3.66–4.94 (4H, m), 6.25 (1H, d, J=15 Hz), 6.88 (1H, dd, J=15, 7.5 Hz), 7.10 (2H, t, J=7.5 Hz), 7.72–7.84 (2H, m)

MASS (ES+) (m/z): 292

EXAMPLE 5

To a solution of N-piperazinyl-p-fluorobenzamide hydrobromide (300 mg), cinnamic acid (161 mg), and 1-hydroxybenzotriazole (173 mg) in N,N-dimethylformamide (6 ml) was added N-ethyl-N'-(3-dimethylaminopropyl)carbodiimide hydrochloride (246 mg) and triethylamine (0.28 ml) at 5° C. The mixture was stirred at 5° C. for 1 hour, and then poured into ethyl acetate and brine. The organic layer was separated, dried over magnesium sulfate, and concentrated. The residue was crystallized from ethyl acetate-diethyl ether to give N-(4-cinnamoyl-1-piperazinyl)-p-fluorobenzamide (0.14 g).

mp: 235–240° C.

NMR (CDCl$_3$, δ): 3.20 (4H, m), 3.96 (4H, m), 6.85 (1H, d, J=15 Hz), 7.15 (2H, dd, J=8, 7.5 Hz), 7.32–7.42 (3H, m), 7.46–7.56 (2H, m), 7.70 (1H, d, j=15 Hz), 7.76–7.86 (2H, m)

MASS (ES+) (m/z): 354

EXAMPLE 6

The following compounds were obtained according to a similar manner to that of Example 5.

1) N-(4-p-Dimethylaminobenzoyl-1-piperazlnyl)-p-fluorobenzamide mp: 240–241° C.

NMR (CDCl$_3$, δ): 2.98 (4H, m), 3.02 (6H, s), 3.85 (4H, m), 6.77 (2H, m), 7.06 (1H, m), 7.1 (2H, dd, J=8, 7.5 Hz), 7.39 (2H, d, J=8 Hz), 7.74–7.81 (2H, m)

MASS (ES+) (m/z): 371

2) N-(4-Phenylpropioloyl-1-piperazinyl)-p-fluorobenzamide mp: 241–242° C.

NMR (CDCl$_3$, δ): 3.00–3.17 (4H, m), 3.85–4.10 (4H, m), 7.12 (2H, dd, J=8, 7.5 Hz), 7.31–7.45 (3H, m), 7.52 (2H, d, J=7.5Hz), 7.75–7.85 (2H, m)

3) N-[4-(6-Methylnicotinoyl)-1-piperazinyl]-p-fluorobenzamide mp: 195–199° C.

NMR (CDCl$_3$, δ): 2.67 (3H, s), 2.93–3.15 (4H, m), 3.57–4.04 (4H, m), 7.08–7.16 (3H, m), 7.31 (1H, d, J=8 Hz), 7.73–7.82 (3H, m), 8.59 (1H, d, J=3.5 Hz)

4) N-[4-Phenylglyoxyloyl-1-piperazinyl]-p-fluorobenzamide mp: 210–212° C.

NMR (CDCl$_3$, δ): 3.04 (2H, br s), 3.15 (2H, br s), 3.56 (2H, br s), 3.98 (2H, br s), 7.10 (2H, d, J=8, 7.5 Hz), 7.53 (2H, t, J=7.5 Hz), 7.63–7.79 (3H, m), 7.96 (2H, d, J=8 Hz)

5) N-[4-(6-Hydroxy-2,5,7,8-tetramethylchroman-2-carbonyl)-1-piperazinyl]-p-fluorobenzamide mp: 175–180° C.

NMR (CDCl$_3$, δ): 1.60 (3H, s), 1.66–1.78 (1H, m), 2.06 (3H, s), 2.11 (3H, s), 2.15 (3H, s), 2.50–2.63 (2H, m), 2.67–2.82 (3H, m), 2.92–3.10 (2H, m), 3.64–3.83 (2H, br s), 4.04–4.18 (1H, br s), 4.25–4.47 (2H, br s), 7.03–7.13 (3H, m), 7.70–7.80 (2H, m)

6) N-[4-(4-Vinylbenzoyl)-1-piperazinyl]-4-fluorobenzamide mp: 216–217° C.

NMR (DMSO-d$_6$, δ): 2.92 (4H, br s), 3.40–3.79 (4H, m), 5.36 (1H, d, J=8.5 Hz), 5.93 (1H, d, J=17 Hz), 6.79 (1H, dd, J=17, 8.5 Hz), 7.32 (2H, t, J=7.5 Hz), 7.48 (4H, ABq, J=8, 7.5 Hz), 7.86 (2H, dd, J=8, 7.5 Hz), 9.61 (1H, s)

7) N-[4-(4-Ethynylbenzoyl)-1-piperazinyl-4-fluorobenzamide mp: 219.5–220.5° C.

NMR (DMSO-d$_6$, δ): 2.92 (4H, br s), 3.43 1(2H, br s), 3.72 (2H, br s), 4.34 (1H, s), 7.31 (1H, dd, J=7.5, 7.5 Hz), 7.50 (2H, ABq, J=7.5, 7.5 Hz), 7.81–7.88 (1H, m), 9.63 (1H, s)

8) N-[4-(4-Phenoxybenzoyl)-1-piperazinyl]-4-fluorobenzamide mp: 213–214° C.

NMR (DMSO-d$_6$, δ): 2.90 (4H, br s), 3.60 (4H, br s), 7.01–7.11 (4H, m), 7.20 (1H, t, J=7.5 Hz), 7.29 (2H, t, J=7.5 Hz), 7.41–7.58 (4H, m), 7.81–7.86 (2H, m), 9.61 (1H, s)

9) N-[4-(4-Acetamidobenzoyl)-1-piperazinyl]-4-fluorobenzamide mp: 230–231.5° C.

NMR (DMSO-d$_6$, δ): 2.07 (3H, s), 2.90 (4H, br s), 3.60 (4H, br s), 7.29 (2H, t, J=7.5 Hz), 7.36 (2H, d, J=7.5 Hz), 7.82–7.88 (2H, m), 9.60 (1H, s)

10) Methyl 4-[4-(1-(4-fluorobenzoylamino)piperazinyl)-carbonyl]benzoate
mp: 207–208° C.
NMR (DMSO-$d_6$, δ): 2.84 (2H, br s), 2.96 (2H, br s), 3.39 (2H, br s), 3.73 (2H, br s), 3.88 (3H, s), 7.28 (1H, t, J=7.5 Hz), 7.54 (1H, d, J=7.5 Hz), 7.80–7.86 (1H, s), 8.04 (1H, d, J=7.5 Hz), 9.62 (1H, s)

11) N-[4-(4-(Methylthiobenzoyl)-1-piperazinyl]-4-fluorobenzamide
mp: 224–225° C.
NMR (CDCl$_3$, δ): 2.50 (3H, s), 3.01 (4H, br s), 3.80 (4H, br s), 6.94 (1H, br s), 7.13 (2H, br s), 7.25–7.30 (2H, m), 7.38 (2H, br s), 7.76 (2H, br s)

12) N-[4-(4-Nitrobenzoyl)-1-piperazinyl]-4-fluorobenzamide
mp: 197–198° C.
NMR (DMSO-$d_6$, δ): 2.85 (2H, br s), 3.00 (2H, br s), 3.40 (2H, br s), 3.76 (2H, br s), 7.30 (2H, t, J=7.5 Hz), 7.69 (2H, d, J=7.5 Hz), 7.80–7.88 (2H, m), 8.32 (2H, d, J=7.5Hz), 9.66 (1H, s)

13) N-[4-(4-Methylsulfonyl)benzoyl)-1-piperazinyl]-4-fluorobenzamide
mp: 282–283° C.
NMR (DMSO-$d_6$, δ): 2.86 (2H, br s), 3.00 (2H, br s), 3.29 (3H, s), 3.39 (2H, br s), 3.75 (2H, br s), 7.20 (2H, t, J=7.5 Hz), 7.68 (2H, t, J=7.5 Hz), 7.81–7.88 (2H, m), 8.03 (2H, d, J=7.5 Hz), 9.65 (1H, s)

14) N-[4-(4-Hydroxybenzoyl)-1-piperazinyl]-4-fluorobenzamide
mp: 237–238° C.
NMR (DMSO-$d_6$, δ): 2.89 (4H, br s), 3.59 (4H, br s), 6.80 (2H, d, J=7.5 Hz), 7.26–7.32 (4H, m), 7.81–7.88 (2H, m), 9.60 (1H, s), 9.89 (1H, br s)

EXAMPLE 7

To a solution of 1-acetyl-4-aminopiperazine dihydrochloride (300 mg), 6-hydroxy-2,5,7,8-tetramethylchroman-2-carboxylic acid (382 mg), 1-hydroxybenzotriazole (244 mg) in N,N-dimethylformamide (6 ml) was added N-ethyl-N'-(3-dimethylaminopropyl)carbodimide hydrochloride (350 mg) and triethylamine (0.78 ml) at 5° C. The mixture was stirred at 5° C. for 2 hours and then poured into ethyl acetate and brine. The organic layer was combined, dried over magnesium sulfate, and concentrated. The residue was crystallized from ethyl acetate to give N-(4-acetyl-1-piperazinyl)-6-hydroxy-2,5,7,8-tetramethylchroman-2-carboxamide (0.17 g).
mp: 212–216° C.
NMR (CDCl$_3$, δ): 1.37 (3H, s), 1.66–1.77 (2H, m), 1.97 (3H, s), 1.99 (3H, s), 2.07 (3H, s), 2.09 (3H, s), 2.10–2.20 (2H, m), 2.58–2.73 (4H, m), 3.38–3.46 (4H, m), 7.50 (1H, s), 8.34 (1H, s)

EXAMPLE 8

The following compounds were obtained according to a similar manner to that of Example 7.

1) N-(4-Acetyl-1-piperazinyl)-6-methylpyridine-3-carboxamide
mp: 170–175° C.
NMR (DMSO-$d_6$, δ): 2.03 (3H, s), 2.51 (3H, s), 2.82 (2H, dd, J=6, 3 Hz), 2.88 (2H, dd, J=6, 3 Hz), 3.49–3.56 (4H, m), 7.35 (1H, d, J=8.3 Hz), 8.00 (1H, dd, J=8.3, 1.5 Hz), 8.80 (1H, d, J=1.5 Hz), 9.67 (1H, s)

2) N-(4-Acetyl-1-piperazinyl)-4-vinylbenzamide
mp: 198–200° C.
NMR (CDCl$_3$, δ): 2.12 (3H, s), 2.96–3.10 (4H, m), 3.66 (2H, br s), 3.83 (2H, br s), 5.38 (1H, d, J=11.5 Hz), 5.83 (1H, d, J=16.5 Hz), 6.74 (1H, dd, J=16.5, 11.5 Hz), 7.18 (1H, br s), 7.46 (2H, d, J=8 Hz), 7.72 (2H, d, J=8 Hz)

3) N-(4-Acetyl-1-piperazinyl)cinnamoylamide
mp: 217–218° C.
NMR (DMSO-$d_6$, δ): 2.12 (3H, s), 2.70–2.84 (4H, m), 3.50 (4H, br s), 6.53 (1H, d, J=16 Hz), 7.34–7.51 (3H, m), 7.53–7.59 (2H, m), 7.63–7.66 (1H, m), 9.23 (1H, s)

4) N-(4-Acetyl-1-piperazinyl)phenylpropioloylamide
mp: 168–169° C.
NMR (CDCl$_3$, δ): 2.12 (3H, s), 2.82–3.00 (4H, m), 3.56–3.83 (4H, m), 7.32–7.46 (3H, m), 7.51–7.59 (2H, m)

5) N-(4-Acetyl-1-piperazinyl)-5-fluoroindole-2-carboxyamide
mp: 290–295" C
NMR (DMSO-$d_6$, δ): 2.03 (3H, s), 2.82–2.95 (4H, m), 3.53 (4H, br s), 7.18 (1H, br s), 6.98–7.09 (2H, m), 7.35–7.44 (2H, m), 9.60 (1H, s)

6) N-(4-Acetyl-1-piperazinyl)-4-dimethylaminobenzamide
mp: 203–205° C.
NMR (CDCl$_3$, δ): 2.10 (3H, s), 2.90–3.03 (4H, m), 3.04 (6H, s), 3.63 (2H, br s), 3.80 (2H, br s), 6.69 (2H,, d, J=8 Hz), 6.97 (1H, br s), 7.58 (2H, d, J=8 Hz)

7) N-(4-Acetyl-1-piperazinyl)quinoline-2-carboxamide
mp: 194–196° C.
NMR (CDCl$_3$, δ): 2.15 (3H, s), 3.04 (2H, t, J=6 Hz), 3.09 (2H, t, J=6 Hz), 3.70 (2H, ., J=6 Hz), 3.87 (2H, t, J=6 Hz), 7.65 (1H, t, J=7.5 Hz), 7.70 (1H, t, J=7.5 Hz), 7.90 (1H, d, J=7.5 Hz), 8.10 (1H, d, J=7.5 Hz), 8.30–8.36 (2H, m), 9.05 (1H, s)

8) N-(4-Acetyl-1-piperazinyl)-4-phenoxybenzamide
mp: 180–182° C.
NMR (CDCl$_3$, δ): 2.12 (3H, s), 2.90–3.00 (4H, m), 3.60–3.68 (2H, m), 3.77–3.83 (2H, m), 6.86 (1H, br s), 6.98–7.06 (4H, m), 7.19 (1H, t, J=7.5 Hz), 7.39 (2H, t, J=7.5 Hz), 7.71 (2H, d, J=7.5 Hz)

9) Methyl 4-[N-(4-acetyl-1-piperazinyl)carbamoyl]benzoate
mp: 233–235° C.
NMR (DMSO-$d_6$, δ): 2.02 (3H, s), 2.83 (2H, t, j=5 Hz), 2.89 (2H, t, J=5 Hz), 3.53 (4H, t, J=5 Hz), 3.90 (3H, s), 7.95 (4H, ABq, J=8, 7.5 Hz), 9.75 (1H, s)

10) N-(4-Acetyl-1-piperazinyl)-4-acetamidobenzamide
mp: 269–272° C. (dec.)
NMR (DMSO-$d_6$, δ): 2.00 (3H, s), 2.05 (3H, s), 2.82 (2H, t, J=5 Hz), 2.89 (2H, t, J=5 Hz), 3.54 (4H, br s), 7.68 (4H, ABq, J=8, 8 Hz), 9.41 (1H,. s)

11) N-(4-Acetyl-1-piperazinyl)-2-hydroxy-2-phenylacetamide
NMR (CDCl$_3$, δ): 2.10 and 2.05 (total 3H, s and s), 2.83–2.91 (4H, m), 3.57–3.63 (2H, m), 3.80–3.88 (2H, m), 5.08 (1H, s), 5.39 (1H, s), 6.29 (1H, s), 7.34–7.41 (5H, m)

12) N-(4-Acetyl-1-piperazinyl)quinoline-8-carboxamide
mp: 156–158° C.
NMR (DMSO-$d_6$, δ): 2.05 (3H, s), 2.96 (2H, t, J=5 Hz), 3.03 (2H, t, J=5 Hz), 3.68 (4H, br s), 6.86 (4H, br s), 7.65–7.77 (2H, m), 8.20 (1H, d, J=7.5 Hz), 8.47 (1H, d, J=7.5 Hz), 8.57 (1H, d, J=7.5 Hz), 9.05 (1H, d, J=7.5 Hz)

13) N-(4-Acetyl-1-piperazinyl)-4-methoxybenzamide
mp: 223–224° C.
NMR (DMSO-$d_6$, δ): 2.01 (3H, s), 2.80 (2H, t, J=6 Hz), 2.87 (2H, t, J=6 Hz), 3.50 (4H, br s), 3.80 (3H, s), 6.97 (2H, d, J=7.5 Hz), 7.75 (2H, d, J=7.5 Hz), 9.39 (1H, s)

14) N-(4-Acetyl-1-piperazinyl)phenylglyoxylamide
NMR (DMSO-$d_6$, δ): 2.01 (3H, s), 2.80 (2H, t, J=6 Hz), 2.87 (2H, t, J=6 Hz), 3.50 (4H, br s), 3.80 (3H, s), 6.97 (2H, d, J=7.5 Hz), 7.75 (2H, d, J=7.5 Hz), 9.39 (1H, s)

15) N-(4-Acetyl-1-piperazinyl)-4-ethynylbenzamide
mp: 250–251° C. (dec.)

NMR (DMSO-d$_6$, δ): 2.01 (3H, s), 2.80 (2H, t, J=6 Hz), 2.86 (2H, t, J=6 Hz), 3.52 (4H, br s), 4.39 (1H, s), 7.56 (2H, d, J=8 Hz), 7.79 (2H, d, J=8 Hz), 9.64 (1H, s)

16) N-(4-Acetyl-1-piperazinyl)quinoxaline-6-carboxamide
mp: 220–221.5° C.
NMR (DMSO-d$_6$, δ): 2.05 (3H, s), 2.88 (2H, t, J=6 Hz), 2.98 (2H, t, J=6 Hz), 3.59 (4H, t, J=6 Hz), 7.65 (1H, t, J=7.5 Hz), 8.20 (2H, s), 8.55 (1H, s), 9.05 (2H, s), 9.95 (1H, s)

17) N-(4-Acetyl-1-piperazinyl)-4-(methylthio)benzamide
mp: 244–246° C.
NMR (DMSO-d$_6$, δ): 2.03 (3H, s), 2.50 (3H, s), 2.82 (2H, t, J=7 Hz), 2.89 (2H, t, J=6 Hz), 3.52 (4H, t, J=6 Hz), 7.30 (2H, d, J=7.5 Hz), 7.72 (2H, d, J=7.5 Hz), 9.50 (1H, s)

18) N-(4-Acetyl-1-piperazinyl)-4-(methylsulfonyl)benzamide
mp: 256–258° C.
NMR (DMSO-d$_6$, δ): 2.04 (3H, s), 2.83 (2H, t, J=6.5 Hz), 2.89 (2H, t, J=6.5 Hz), 3.27 (3H, s), 3.53 (4H, t, J=6.5 Hz), 7.87 (1H, d, J=7.5 Hz), 7.97–8.09 (3H, m), 9.80 (1H, s)

19) N-(4-Acetyl-1-piperazinyl)-4-hydroxybenzamide
mp: 298–299° C. (dec.)
NMR (DMSO-d$_6$, δ): 2.00 (3H, s), 2.80 (2H, br s), 2.88 (2H, br s), 3.50 (4H, br s), 6.79 (2H, d, J=7.5 Hz), 7.65 (2H, d, J=7.5 Hz), 9.30 (1H, s), 9.99 (1H, s)

20) N-(4-Acetyl-1-piperazinyl)-5-chloro-3-phenylbenzofuran-2-carboxamide
mp: 221–222° C.
NMR (DMSO-d$_6$, δ): 2.00 (3H, s), 2.79 (2H, t, J=5 Hz), 2.83 (2H, t, J=5 Hz), 3.50 (4H, br s), 7.45–7.62 (7H, m), 7.78 (1H, d, J=7.5 Hz), 9.87 (1H, s)

EXAMPLE 9

To a stirred solution of N-piperazinyl-p-fluorobenzamide hydrobromide (300 mg) and triethylamine (0.41 ml) in dichloromethane (6 ml) was added 4-cyanobenzoyl chloride (196 mg) at 0° C. The mixture was stirred at ambient temperature for 3 hours, diluted with ethyl acetate and washed with water (×2). The organic layer was separated, dried over magnesium sulfate, and concentrated. The crystal residue was recrystallized from methanol, ethyl acetate and n-hexane to give N-[4-(4-cyanobenzoyl)-1-piperazinyl]-4-fluorobenzamide (199 mg).

mp: 222–223.5° C.
NMR (CDCl$_3$, δ): 2.99 (2H, br s), 3.11 (2H, br s), 3.54 (2H, br s), 3.97 (2H, br s), 7.00 (1H, br s), 7.13 (2H, t, J=7.5 Hz), 7.53 (2H, d, J=7.5 Hz), 7.71–7.77 (4H, m)

EXAMPLE 10

The following compound was obtained according to a similar manner to that of Example 9.

N-[4-(4-Phenylbenzoyl)-1-piperazinyl]-4-fluorobenzamide
mp: 265° C.
NMR (CDCl$_3$, δ): 2.93 (4H, br s), 3.30 (4H, br s), 3.54 (2H, br s), 7.30 (2H, t, J=7.5 Hz), 7.39–7.51 (5H, m), 7.69–7.77 (4H, m), 7.83–7.88 (2H, m), 9.63 (1H, s)

EXAMPLE 11

To a solution of 1-acetyl-4-aminopiperazine dihydrochloride (300 mg) in dichloromethane (9 ml) was added triethylamine (0.77 ml) and phenyl chloroformate (0.261 ml) at ambient temperature. The mixture was stirred at the same temperature for 1 hour, and washed with water (×2). The organic layer was separated, dried over magnesium sulfate, and concentrated. The residue was crystallized from ethyl acetate and diethyl ether to give phenyl N-(4-acetyl-1-piperazinyl)carbamate (0.29 g).

mp: 162–163° C.
NMR (CDCl$_3$, δ): 2.12 (3H, s), 2.97 (4H, br s), 3.62 (2H, br s), 3.77 (2H, br s), 6.28 (1H, br s), 7.09–7.16 (2H, m), 7.19–7.25 (1H, m), 7.32–7.40 (2H, m)

EXAMPLE 12

The following compounds were obtained according to a similar manner to that of Example 11.

1) N-(4-Acetyl-1-piperazinyl)-4-trifluoromethoxybenzamide
mp: 185–188° C.
NMR (CDCl$_3$, δ): 2.13 (3H, s), 3.05 (4H, br s), 3.68 (2H, br s), 3.83 (2H, br s), 7.27 (2H, d, j=8 Hz), 7.47 (1H, br s), 7.82 (2H, d, J=8 Hz)

2) N-(4-Acetyl-1-piperazinyl)-4-trifluoromethylbenzamide
mp: 203–206° C.
NMR (CDCl$_3$, δ): 2.12 (3H, s), 2.96–3.10 (4H, m), 3.68 (2H, br s), 3.83 (2H, br s), 7.50 (1H, br s), 7.70 (2H, d, J=8 Hz), 7.89 (2H, d, J=8 Hz)

EXAMPLE 13

To a stirred solution of 1-acetyl-4-aminopiperazine dihydrochloride (250 mg) and triethylamine (0.65 ml) in dichloromethane (9 ml) was added 2-thiophenecarbonyl chloride (0.19 ml) at 0° C. The mixture was stirred at ambient temperature for 1 hour, diluted with ethyl acetate and washed with water (×2). The organic layer was separated, dried over magnesium sulfate, and concentrated. The residue was purified by column chromatography eluting with a mixture of methanol and ethyl acetate (1:10) to give crystals. Recrystallization from ethanol gave N-(4-acetyl-1-piperazinyl)thiophene-2-carboxamide (256 mg).

mp: 211.5–213° C.
NMR (CDCl$_3$, δ): 2.11 (3H, s), 2.54–2.78 (3H, m), 2.87–3.20 (3H, mq), 3.50–3.85 (2H, m), 4.59–4.63 (1H, m), 7.12 (1H, br s), 7.58 (1H, br s), 8.09 (1H, br s)

EXAMPLE 14

The following compounds were obtained according to a similar manner to that of Example 13.

1) N-(4-Acetyl-1-piperazinyl)-4-nitrobenzamide
mp: 201–202.5° C.
NMR (CDCl$_3$, δ): 2.13 (3H, s), 2.97, (4H, br s), 3.69 (2H, br s), 3.80 (2H, br s), 7.98 (2H, d, J=7.5 Hz), 8.29 (2H, d, J=7.5 Hz)

2) N-(4-Acetyl-1-piperazinyl)-4-phenylbenzamide
mp: 247–248.5° C.
NMR (DMSO-d$_6$, δ): 2.04 (3H, s), 2.85 (2H, t, J=6 Hz), 2.90 (2H, t, J=7 Hz), 3.53 (2H, br s), 7.39–7.52 (3H, m), 7.72–7.89 (6H, m), 9.60 (1H, s)

3) N-(4-Acetyl-1-piperazinyl)-4-cyanobenzamide
mp: 219–220° C.
NMR (DMSO-d$_6$, δ): 2.03 (3H, s), 2.83 (2H, t, J=6 Hz), 2.89 (2H, t, J=7 Hz), 3.53 (4H, t, J=6 Hz), 7.95 (4H, ABq, J=7.5, 7.5 Hz), 9.80 (1H, s)

4) N-(4-Acetyl-1-piperazinyl)-N'-methyl-N'-phenylurea
NMR (CDCl$_3$, δ): 2.04 (3H, s), 2.70 (2H, t, J=6 Hz), 2.75 (2H, , J=6 Hz), 3.28 (3H, s), 3.47 (2H, t, J=6 Hz), 3.64 (2H, t, J=6 Hz), 5.24 (1H, s), 7.20–7.45 (5H, m)

EXAMPLE 15

To a solution of 1-acetyl-4-aminopiperazine dihydrochloride (250 mg) in 1N aqueous solution of sodium hydroxide (3.5 ml) and dioxane (3.5 ml) was added piperonyloyl chloride (320 mg) at ambient temperature, and the mixture was stirred at the same temperature for 1 hour. After removal of the organic solvent in vacuo, the residue was collected, washed with water and ethyl acetate. The residue was crystallized from 20% ethanol in water to give N-(4-acetyl-1-piperazinyl)piperonyloylamide (0.15 g).

mp: 197–200° C.

NMR (DMSO-$d_{61}$, $\delta$): 2.01 (3H, s), 2.80 (2H, m), 2.86 (2H, m), 3.54 (4H, m), 6.09 (2H, s), 6.98 (1H, d, J=8 Hz), 7.30 (1H, s), 7.36 (1H, d, J=BHz), 9.39 (1H, s)

EXAMPLE 16

To a stirred solution of 1-aminohomopiperazine-4-benzyloxycarbonyl (690 mg) and triethylamine (0.77 ml) in dichloromethane (5 ml) was added 4-fluorobenzoyl chloride (0.33 ml) at 0° C. The mixture was stirred at ambient temperature for 1 hour, washed with 1N hydrochloric acid, water, saturated aqueous solution of sodium hydrogen carbonate, water and brine. The organic layer was dried over magnesium sulfate and concentrated. The residue was purified by column chromatography eluting with a mixture of ethyl acetate and n-hexane (2:1) to give N-(4-benzyloxycarbonyl-1-homopiperazinyl)-4-fluorobenzamide (716 mg).

mp: 116–118° C.

NMR (CDCl$_3$, $\delta$): 2.03 (2H, br s), 3.35 (4H, br s), 3.57–3.78 (4H, m), 5.17 (2H, s), 7.10 (3H, t, J=7.5 Hz), 7.30–7.39 (5H, m), 7.75 (2H, br s)

EXAMPLE 17

To a stirred solution of rac-N-benzyl-1-acetyl-4-aminopiperazine-2-carboxamide (274 mg) and triethylamine (0.28 ml) in dichloromethane (5 ml) was added 4-fluorobenzoyl chloride (0.13 ml) at 0° C. The mixture was stirred at ambient temperature for 1 hour, washed with water and brine. The organic layer was dried over magnesium sulfate, and concentrated. The residue was purified by column chromatography eluting with a mixture of methanol and chloroform (1:9) to give crystals. Recrystallization of methanol, ethyl acetate and n-hexane gave rac-N-[4-acetyl-3-(N-benzylcarbamoyl)-1-piperazinyl]-4-fluorobenzamide (104 mg).

mp: 116–118° C.

NMR (DMSO-$d_6$, $\delta$): 2.08 (3H, d, J=7 Hz), 2.78–2.84 (1H, m), 2.92–3.07 (3H, m), 3.40–3.58 (2H, m), 3.75–3.83 (1H, m), 4.29–4.42 (2H, m), 7.20–7.33 (6H, m), 7.84–7.91 (2H, m), 8.50 (1H, t, J=7 Hz), 9.24 (1H, t, J=7 Hz), 9.79 (1H, s)

EXAMPLE 18

To a stirred solution of (S)-1-acetyl-4-amino-2-methylpiperazine (320 mg) and triethylamine (0.57 ml) in dichloromethane (10 ml) was added 4-fluorobenzoyl chloride (0.27 ml) at 0° C. The mixture was stirred at ambient temperature for 3 hours, washed with water and brine. The organic layer was dried over magnesium sulfate, and concentrated. The residue was purified by column chromatography eluting with a mixture of methanol and chloroform (1:9) to give (S)-N-(4-acetyl-2-methyl-1-piperazinyl)-4-fluorobenzamide (50 mg).

NMR (CDCl$_3$, $\delta$): 1.39 (1H, s), 1.49 (2H, s), 2.10 (3H, s), 2.71–2.80 (1H, m), 2.86–3.08 (2H, m), 3.13–3.25 (2H, m), 3.56–3.69 (0.5H, m), 4.09 (0.5H, s), 4.48–4.60 (0.5H, m), 4.90 (0.5H, s), 7.03 (1H, s), 7.13 (2H, t, J=7 Hz), 7.78 (2H, t, J=7 Hz)

EXAMPLE 19

To a solution of 1-acetyl-4-aminopiperazine dihydrochloride (300 mg) in ethanol (10 ml) and triethylamine (0.78 ml) was added p-fluorobenzaldehyde (0.164 ml), and the mixture was heated at 80° C. for 2 hours. After removal of the solvent in vacuo, the residue was triturated with ethyl acetate and water. The organic layer was separated, dried over magnesium sulfate, and concentrated. The residue was crystallized from diisopropyl ether to give 1-acetyl-4-(4-fluorobenzylidene)aminopiperazine (0.15 g).

mp: 88–90° C.

NMR (CDCl$_3$, $\delta$): 2.13 (3H, s), 3.08–3.25 (4H, m), 3.62–3.72 (2H, m), 3.77–3.86 (2H, m), 7.06 (2H, t, J=8 Hz), 7.53–7.68 (3H, m)

EXAMPLE 20

To a solution of N-piperazinyl-p-fluorobenzamide hydrobromide (300 mg) and triethylamine (0.412 ml) in dichloromethane (6 ml) was added phenyl isocyanate (0.186 ml) at ambient temperature, and the reaction mixture was stirred at the same temperature for 1 hour. The precipitate was filtered, then washed with dichloromethane and water. The residue was dried to give N-(4-phenylcarbamoyl-1-piperazinyl)-p-fluorobenzamide (0.23 g).

mp: 263–266° C.

NMR (DMSO-$d_6$, $\delta$): 2.87–2.93 (4H, m), 3.52–3.57 (4H, m), 6.93 (1H, d, J=7.5 Hz), 7.23 (2H, t, J=7.5 Hz), 7.30 (2H, t, J=8 Hz), 7.46 (2H, d, J=8 Hz), 7.85 (2H, dd, J=8, 7.5 Hz), 8.59 (1H, s), 9.55 (1H, s)

EXAMPLE 21

To a solution of di-tert-butyl dicarbonate (33 g) in dichloromethane (350 ml) was added dropwise 1-benzyloxycarbonyl-4-aminopiperazine (35 g) in dichloromethane (350 ml) at 5° C. After removal of the solvent, ethyl acetate (600 ml) was added and the mixture was triturated. The precipitate was filtered off and washed with ethyl acetate. The filtrate was washed with 1N hydrochloric acid, saturated aqueous solution of sodium hydrogen carbonate, and brine. The organic layer was collected, dried over magnesium sulfate, and filtered. After removal of the solvent in vacuo, the residue was crystallized from diisopropyl ether to give N-(4-benzyloxycarbonyl-1-piperazinyl)-tert-butoxycarboxamide (29.5 g).

mp: 125–126° C.

NMR (CDCl$_3$, $\delta$): 1.45 (9H, s), 2.79 (4H, br s), 3.62 (4H, m), 5.13 (2H, s), 5.57 (1H, s), 7.30–7.38 (5H, m)

EXAMPLE 22

To a solution of N-(1-homopiperazinyl)-4-fluorobenzamide hydrobromide (455 mg) in 1N aqueous solution of sodium hydroxide (3.2 ml) was added acetic anhydride (0.2 ml) at 0° C., and the solution was stirred at ambient temperature for 1.5 hours. The reaction mixture was extracted with a mixture of ethyl acetate and n-butanol. The organic layer was washed with brine, dried over magnesium sulfate, and concentrated. The residue was purified by column chromatography eluting with a mixture of methanol and ethyl acetate (1:15) to give oil. The oil was crystallized when treated with ethyl acetate below 0° C. to give N-(4-acetyl-1-homopiperazinyl)-4-fluorobenzamide (137 mg).

mp: 117–119° C.

NMR (CDCl$_3$, $\delta$): 1.79 (1H, quintet, J=7 Hz), 1.89 (1H, quintet, J=7 Hz), 2.12 (3H, s), 3.03–3.09 (3H, m), 3.15 (1H, t, J=7 Hz), 3.50 (2H, t, J=7 Hz), 3.53 (2H, t, J=7 Hz), 7.25–7.30 (2H, m), 7.80–7.87 (2H, m), 9.82 (1H, d, J=15 Hz)

EXAMPLE 23

To a solution of N-(1-piperazinyl)-tert-butoxycarboxamide (15 g) in dichloromethane (200 ml) was added acetic anhydride (7.74 ml) and pyridine (6.63 ml). The mixture was stirred at ambient temperature for 1 hour. The solution was washed with saturated aqueous solution of sodium hydrogen carbonate and brine. The organic layer was collected, dried over magnesium sulfate, and concentrated. The residue was triturated with n-hexane to give N-(4-acetyl-1-piperazinyl)-tert-butoxycarboxamide (16.4 g).

mp: 128–129° C.

NMR (CDCl$_3$, δ):1.46 (9H, s), 2.08 (3H, s), 2.75–2.83 (4H, m), 3.51–3.57 (2H, m), 3.67–3.73 (2H, m), 5.57 (1H, s)

EXAMPLE 24

To a stirred mixture of N-(4-acetyl-1-piperazinyl)-4-fluorobenzamide (230 mg) and N,N-dimethylformamide (3 ml) was added sodium hydride (60% oil dispersion, 35 mg) in one portion at 0° C. The mixture was stirred at 0° C. for 1 hour then benzyl bromide (0.17 ml) was added to this mixture at 0° C. After stirring at 0° C. for 1.5 hours, water was added and the solvent was evaporated. The residue was taken up in ethyl acetate, washed with brine, dried over magnesium sulfate and concentrated. The residue was purified by column chromatography eluting with a mixture of methanol and ethyl acetate (1:5) to give crystals. Crystallization from ethyl acetate and n-hexane to give N-(4-acetyl-1-piperazinyl)-N-benzyl-4-fluorobenzamide (260 mg).

mp: 180–181° C.

NMR (CDCl$_3$, δ): 2.09 (3H, s), 2.83 (2H, ddd, J=9, 9, 3 Hz), 3.52 (1H, t, J=13 Hz), 3.66 (1H, d, J=13 Hz), 3.99 (1H, t, J=13 Hz), 4.21–4.29 (1H, m), 4.54 (1H, d, J=13 Hz), 4.63–4.72 (1H, m), 5.15 (2H, ,d, J=3 Hz), 7.02 (2H, t, J=7.5 Hz), 7.39–7.46 (5H, m), 7.98–8.02 (2H, m)

EXAMPLE 25

To a stirred solution of methyl 4-[4-(1-(4-fluorobenzoylamino)piperazinyl)carbonyl]benzoate (500 mg) in methanol (10 ml) was added 1N aqueous solution of sodium hydroxide (1.6 ml) at ambient temperature and the mixture was stirred at the same temperature for 5 hours. After evaporation of solvent, the residue was diluted with water and neutralized with 1N hydrochloric acid and extracted with a mixture of ethyl acetate and tetrahydrofuran. The organic layer was dried over magnesium sulfate and concentrated. The residue was recrystallized from methanol, ethyl acetate and n-hexane to give 4-[4-(1-(4-fluorobenzoylamino)piperazinyl)carbonyl]benzoic acid (260 mg).

mp: 270–271° C.

NMR (DMSO-d$_6$, δ): 2.87 (2H, br s), 2.97 (2H, br s), 3.39 (2H, br s), 3.53 (2H, br s), 7.30 (2H, t, J=7.5 Hz), 7.52 (2H, t, J=7.5 Hz), 7.80–7.86 (2H, m), 8.02 (2H, d, J=7.5 Hz), 9.63 (1H, s)

EXAMPLE 26

To a stirred solution of methyl 4-[N-(4-acetyl-1-piperazinyl)carbamoyl]benzoate (300 mg) in methanol (9 ml) was added 1N aqueous solution of sodium hydroxide (1.2 ml) at ambient temperature and the mixture was stirred at the same temperature for 10 hours. After evaporation of solvent, the residue was diluted with water and neutralized with 1N hydrochloric acid and extracted with a mixture of ethyl acetate and tetrahydrofuran. The organic layer was dried over magnesium sulfate and concentrated. The residue was washed with tetrahydrofuran and ethyl acetate to give 4-N-(4-acetyl-1-piperazinyl)carbamoyl]benzoic acid (290 mg).

mp: 314–315° C. (dec.)

NMR (DMSO-d$_6$, δ): 2.87 (2H, br s), 2.97 (2H, br s), 3.39 (2H, br s), 3.53 (2H, br s), 7.30 (2H, t, J=7.5 Hz), 7.52 (2H, t, J=7.5 Hz), 7.80–7.86 (2H, m), 8.02 (2H, d, J=7.5 Hz), 9.63 (1H, s)

EXAMPLE 27

N-[4-(4-Nitrobenzoyl)-1-piperazinyl]-4-fluorobenzamide (254 mg) was hydrogenated over 10% palladium on carbon (73 mg) in methanol (10 ml) at ambient temperature for 4 hours. The catalyst was filtered off over Celite pad and the filtrate was concentrated in vacuo to give crystals. The crystals were recrystallized from methanol, ethyl acetate and n-hexane to give N-[4-(4-aminobenzoyl)-1-piperazinyl]-4-fluorobenzamide (188 mg).

mp: 209° C.

NMR (DMSO-d$_6$, δ): 2.87 (4H, br s), 3.06 (4H, br s), 5.54 (2H, s), 6.54 (2H, d, J=7.5 Hz), 7.12 (2H, d, J=7.5 Hz), 7.29 (2H, t, J=7.5 Hz), 7.80,7.86 (2H, m), 9.56 (1H, s)

What is claimed is:

1. A compound of the formula:

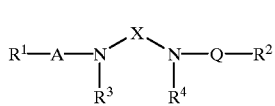

[I]

wherein

R$^1$ is lower alkyl, lower alkenyl, lower alkynyl, cyclo (lower)alkyl, aryl, ar(lower) alkoxy, aryloxy, arylamino or a heterocyclic group, each of which is optionally substituted; or acyl;

R$^2$ is lower alkyl, lower alkenyl, lower alkynyl, cyclo (lower)alkyl, aryl, ar(lower)alkoxy, lower alkoxy, aryloxy or a heterocyclic group, each of which optionally is substituted; or acyl;

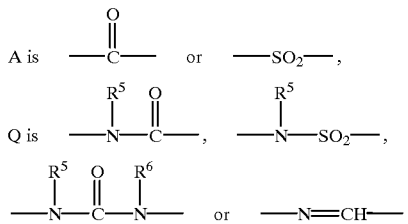

wherein

R$^5$ is hydrogen, lower alkyl, lower alkyl substituted by halogen, aryl, acyl, lower alkoxy or aryloxy, aryl, acyl or a heterocyclic group, and R$^6$ is hydrogen or lower alkyl, X is ethylene optionally substituted, and R$^3$ and R$^4$ taken together form ethylene optionally condensed with a cyclic hydrocarbon or a heterocyclic ring, provided that when R¹ is lower alkyl, aryl, ar(lower)alkoxy or a heterocyclic group, each of which optionally is substituted with halogen, R² is cyclo(lower)alkyl, aryl or ar(lower)alkyl, each of which optionally is substituted with halogen, X is ethylene and R³ and R⁴ taken together form ethylene;

then 1) Q is

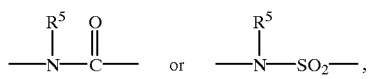

wherein R⁵ is lower alkyl substituted by halogen, aryl, acyl, lower alkoxy or aryloxy, aryl, acyl or a heterocyclic group, or 2) Q is

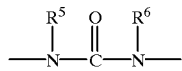

wherein R⁵ is hydrogen, lower alkyl, lower alkyl substituted by halogen, aryl, acyl, lower alkoxy or aryloxy, aryl, acyl or a heterocyclic group, and R⁶ is lower alkyl; or when R¹ is aryl which optionally is substituted with halogen, X is ethylene;

R³ and R⁴ taken together form ethylene; and

R² is lower alkoxy, and

Q is

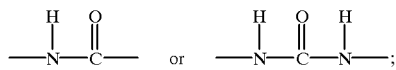

or

R² is aryl, and

Q is —N=CH—;

then A is

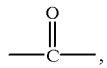

and pharmaceutically acceptable salts thereof.

2. The compound of claim 1, when R¹ as substituted aryl or a substituted heterocyclic group, said substituent for said aryl or heterocyclic group being selected from the group consisting of halo(lower)alkyl, halo(lower)alkoxy, lower alkenyl, lower alkynyl, lower alkylamino, acylamino, acyl, lower alkylsilyl, lower alkoxy, aryl, lower alkylenedioxy, acyloxy, hydroxy, nitro, amino, cyano, aryloxy and lower alkylthio.

3. The compound of claim 1, wherein when R² is a heterocyclic group or substituted aryl, said substituent is selected from the group consisting of halo(lower)alkyl, lower alkenyl, lower alkynyl, lower alkylamino, acyl, lower alkylsilyl, lower alkoxy, aryl, lower alkylenedioxy, acyloxy, hydroxy, cyano, aryloxy, acylamino, nitro, halogen, halo(lower)alkoxy and lower alkylthio.

4. A process for preparing a compound of the formula:

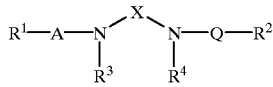

[I]

wherein

R¹ is lower alkyl, lower alkenyl, lower alkynyl, cyclo(lower)alkyl, aryl, ar(lower) alkoxy, aryloxy, arylamino or a heterocyclic group, each of which optionally is substituted; or acyl;

R² is lower alkyl, lower alkenyl, lower alkynyl, cyclo(lower)alkyl, aryl, ar(lower)alkoxy, lower alkoxy, aryloxy or a heterocyclic group, each of which optionally is substituted; or acyl;

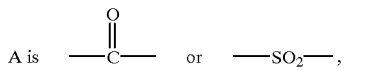

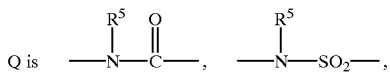

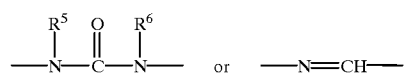

wherein R⁵ is hydrogen, lower alkyl, lower alkyl substituted by halogen, aryl, acyl, lower alkoxy or aryloxy, aryl, acyl or a heterocyclic group, and R⁶ is hydrogen or lower alkyl, X is ethylene optionally substituted, and R³ and R⁴ taken together form ethylene optionally condensed with a cyclic hydrocarbon or a heterocyclic ring, provided that when R¹ is lower alkyl, aryl, ar(lower)alkoxy or a heterocyclic group, each of which is optionally substituted with halogen, R² is cyclo(lower)alkyl, aryl or ar(lower)alkyl, each of which is optionally substituted with halogen, X is ethylene and R³ and R⁴ taken together form ethylene;

then 1) Q is

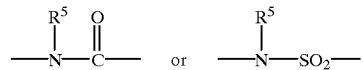

wherein R⁵ is lower alkyl substituted by halogen, aryl, acyl, lower alkoxy or aryloxy, aryl, acyl or a heterocyclic group, or 2) Q is

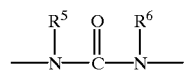

wherein R⁵ is hydrogen, lower alkyl, lower alkyl substituted by halogen, aryl, acyl, lower alkoxy or aryloxy, aryl, acyl or a heterocyclic group, and R⁶ is lower alkyl; or when R¹ is aryl which optionally is substituted with halogen, X is ethylene;
R³ and R⁴ taken together form ethylene; and
R² is lower alkoxy, and
Q is

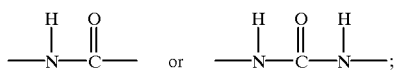

or

R² is aryl, and
Q is —N=CH—;
then A is

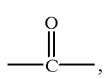

or pharmaceutically acceptable salts thereof, which comprises, a) reacting a compound of the formula:

[II]

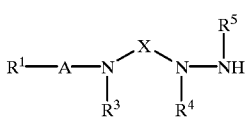

or its salt with a compound of the formula:

HO—Y—R²  [III]

or its reactive derivative at the carboxy or sulfo group, or a salt thereof to provide a compound of the formula:

[Ia]

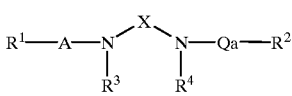

or its salt, in the above formulas, $R^1$, $R^2$, $R^3$, $R^4$, $R^5$, A, Q and X are each as defined above,
Y is

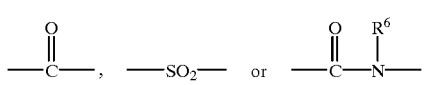

wherein $R^6$ is as defined above, and
Qa is

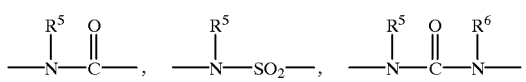

wherein $R^5$ and $R^6$ are each as defined above; or b) reacting a compound of the formula:

[II]

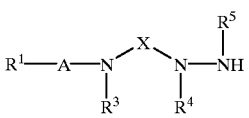

or its salt with a compound of the formula:

$R^2$—NCO  [IV]

to provide a compound of the formula:

[Ib]

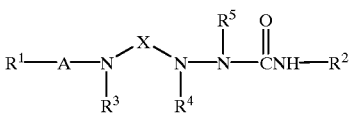

or its salt, in the above formulas, $R^1$, $R^2$, $R^3$, $R^4$, $R^5$, A and X are each as defined above, or c) reacting a compound of the formula:

[Ic]

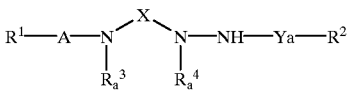

or its salt with a compound of the formula:

$R_a^5$—Z  [V]

to provide a compound of the formula:

[Id]

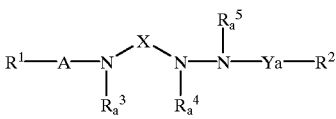

or its salt, in the above formulas, $R^1$, $R^2$, A and X are each as defined above,
$R_a^3$ and $R_a^4$ taken together form ethylene,
$R_a^5$ is lower alkyl or lower alkyl substituted by halogen, aryl, acyl, lower alkoxy or aryloxy,
Ya is

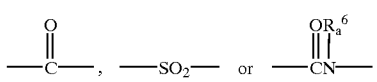

wherein $R_a^6$ is lower alkyl, and

Z is an acid residue; or d) reacting a compound of the formula:

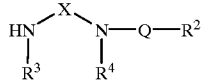

[VI]

or its salt with a compound of the formula:

$R^1$—A—OH

[VII]

or its reactive derivative of the carboxy or sulfo group, or a salt thereof to provide a compound of the formula:

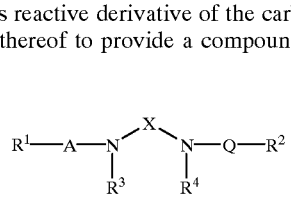

[I]

or its salt, in the above formulas, $R^1, R^2, R^3, R^4, R^5, A, Q$ and X are each as defined above; or e) reacting a compound of the formula:

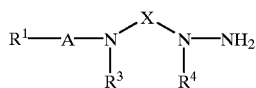

[IIa]

or its salt with a compound of the formula:

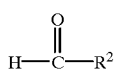

[VIII]

or its salt to provide a compound of the formula:

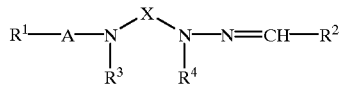

[Ie]

or its salt, in the above formulas, $R^1, R^2, R^3, R^4, A,$ and X are each as defined above; or f) reacting a compound of the formula:

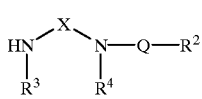

[VI]

or its salts with a compound of the formula:

$R^7$—NCO

[IX]

to provide a compound of the formula:

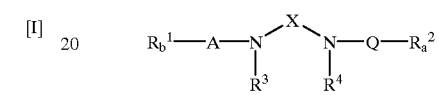

[If]

or its salt, in the above formulas, $R^2, R^3, R^4, Q$ and X are each as defined above, $R^7$ is aryl which is optionally substituted, and $R_a^1$ is arylamino which is optionally substituted; or g) subjecting a compound of the formula:

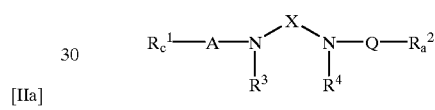

[Ig]

or its salt to deesterification reaction to provide a compound of the formula:

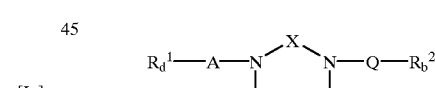

[Ih]

or its salt, in the above formulas, $R^3, R^4, A, Q$ and X are each as defined above, $R_b^1$ is aryl which is substituted with esterified carboxy, $R_c^1$ is aryl which is substituted with carboxy, and $R_a^2$ is aryl which is optionally substituted with halogen; or h) subjecting a compound of the formula:

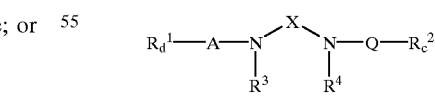

[Ij]

or its salt to deesterification reaction to provide a compound of the formula:

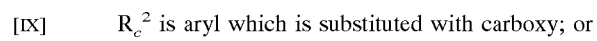

[Ij]

or its salt, in the above formulas, $R^3, R^4, A, Q$ and X are each as defined above, $R_d^1$ is lower alkyl, $R_b^2$ is aryl which is substituted with esterified carboxy, and $R_c^2$ is aryl which is substituted with carboxy; or i) reducing a compound of the formula:

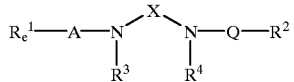
[Ik]

or its salt to provide a compound of the formula:

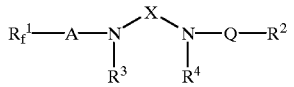
[II]

or its salt, in the above formulas, $R^2$, $R^3$, $R^4$, A, Q and X are each as defined above, $R_e^1$ is aryl which is substituted with nitro, and $R_f^1$ is aryl which is substituted with amino.

5. A pharmaceutical composition comprising the compound of claim 1, as an active ingredient, in association with a pharmaceutically acceptable, substantially non-toxic carrier or excipient.

6. A method for therapeutic treatment of amnesia, dementia or senile dementia which comprises administering an effective amount of a compound of claim 1 to a human subject of mammals.

* * * * *